United States Patent
Lin et al.

(10) Patent No.: US 11,136,360 B2
(45) Date of Patent: Oct. 5, 2021

(54) FUSION PROTEINS COMPRISING A MTU ΔI-CM INTEIN VARIANT AND METHODS OF PROTEIN PURIFICATION

(71) Applicants: Tsinghua University, Beijing (CN); South China University of Technology, Guangzhou (CN)

(72) Inventors: Zhanglin Lin, Guangzhou (CN); Tingting Wang, Guangzhou (CN); Qing Zhao, Shanghai (CN); Xu Wang, Shanghai (CN); Bihong Zhou, Guangzhou (CN); Lei Xing, Beijing (CN)

(73) Assignees: Tsinghua University; South China University of Technology

( * ) Notice: Subject to any disclaimer, the term of this patent is extended or adjusted under 35 U.S.C. 154(b) by 0 days.

(21) Appl. No.: 16/720,456

(22) Filed: Dec. 19, 2019

(65) Prior Publication Data

US 2020/0199183 A1 Jun. 25, 2020

Related U.S. Application Data

(63) Continuation of application No. PCT/CN2018/122075, filed on Dec. 19, 2018.

(51) Int. Cl.
*C07K 14/35* (2006.01)
*C07K 1/14* (2006.01)

(52) U.S. Cl.
CPC .......... *C07K 14/35* (2013.01); *C07K 1/14* (2013.01); *C07K 2319/60* (2013.01); *C07K 2319/92* (2013.01)

(58) Field of Classification Search
None
See application file for complete search history.

(56) References Cited

U.S. PATENT DOCUMENTS

6,933,362 B1 * 8/2005 Belfort .................. C07K 14/35
530/300
9,796,967 B2 10/2017 Ma et al.
2006/0141570 A1 * 6/2006 Wood .................. C07K 14/225
435/69.1
2013/0266583 A1 * 10/2013 Shone .................. A61K 39/40
424/167.1
2014/0106399 A1 * 4/2014 Lin ...................... C12P 21/06
435/68.1

FOREIGN PATENT DOCUMENTS

| CN | 105263509 A | 1/2016 |
| CN | 107406514 A | 11/2017 |
| CN | 108707193 A | 10/2018 |
| WO | WO 01/12820 A1 | 2/2001 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Alignment of SEQ ID No. 1 of the instant application to SEQ ID No. 56 of US20130266583 (Year: 2013).*
Roey et al. J Mol Biol. Mar. 16, 2007;367(1):162-73 (Year: 2007).*
Wood et al. J Biol Chem. May 23, 2014;289(21):14512-9. (Year: 2014).*
Accession BBI97211. Aug. 14, 2014 (Year: 2014).*
Guhan et al. The Journal of Biological Chemistry. vol. 277, No. 43, Issue of Oct. 25, pp. 40352-40361, 2002 (Year: 2002).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Nicastri et al. (2013) "Internal Disulfide Bond Acts as a Switch for Intein Activity," Biochemistry 52(34): 5920-5927.
Wood et al. (1999) "A genetic system yields self-cleaving inteins for bioseparations," Nat. Biotech. 17: 889-892.
International Search Report and Written Opinion dated Sep. 18, 2019, corresponding to International Patent Application No. PCT/CN2018/122075, 22 pp.

* cited by examiner

*Primary Examiner* — Christian L Fronda
(74) *Attorney, Agent, or Firm* — Leydig, Voit & Mayer, Ltd.

(57) ABSTRACT

The present disclosure describes a Mtu ΔI-CM intein variant containing one or more mutations or a biologically active fragment thereof, and a method for producing and purifying a molecule of interest using the intein variant. Further described are isolated fusion proteins comprising the intein variant and a tag and a molecule of interest. Also described are expression systems for expressing the intein variant as well as polypeptide screening methods employing the intein variant.

10 Claims, 9 Drawing Sheets

Specification includes a Sequence Listing.

(d)

(e)

SEQUENCE LISTING

<160> NUMBER OF SEQ ID NOS: 53

<210> SEQ ID NO 1
<211> LENGTH: 168
<212> TYPE: PRT
<213> ORGANISM: Artificial Sequence
<220> FEATURE:
<223> OTHER INFORMATION: Synthetic Construct

<400> SEQUENCE: 1

Ala Leu Ala Glu Gly Thr Arg Ile Phe Asp Pro Val Thr Gly Thr Thr
1               5                   10                  15

```
His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Leu His Thr Leu Val
145                 150                 155                 160

Ala Glu Gly Val Val Val His Asn
                165

<210> SEQ ID NO 2
<211> LENGTH: 168
<212> TYPE: PRT
<213> ORGANISM: Artificial Sequence
<220> FEATURE:
<223> OTHER INFORMATION: Synthetic Construct

<400> SEQUENCE: 2

Ala Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp Tyr Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Leu His Thr Leu Val
145                 150                 155                 160

Ala Glu Gly Val Val Val His Asn
                165

<210> SEQ ID NO 3
<211> LENGTH: 168
<212> TYPE: PRT
<213> ORGANISM: Artificial Sequence
<220> FEATURE:
```

<223> OTHER INFORMATION: Synthetic Construct

<400> SEQUENCE: 3

```
Ala Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp Val Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Thr Leu Val
145                 150                 155                 160

Ala Glu Gly Val Val Val His Asn
                165
```

<210> SEQ ID NO 4
<211> LENGTH: 168
<212> TYPE: PRT
<213> ORGANISM: Artificial Sequence
<220> FEATURE:
<223> OTHER INFORMATION: Synthetic Construct

<400> SEQUENCE: 4

```
Ala Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Asn Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Thr Leu Val
145                 150                 155                 160

Ala Glu Gly Val Val Val His Asn
                165
```

<210> SEQ ID NO 5
<211> LENGTH: 168
<212> TYPE: PRT
<213> ORGANISM: Artificial Sequence
<220> FEATURE:
<223> OTHER INFORMATION: Synthetic Construct

<400> SEQUENCE: 5

```
Ala Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
                20                  25                  30

Ala Ala Ala Lys Asp Gly Thr Leu His Ala Arg Pro Val Val Ser Trp
            35                  40                  45

Phe Asp Gln Gly Thr Arg Asp Val Ile Gly Leu Arg Ile Ala Gly Gly
        50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Ser Glu Leu His Thr Leu Val
145                 150                 155                 160

Ala Glu Gly Val Val Val His Asn
                165
```

<210> SEQ ID NO 6
<211> LENGTH: 168
<212> TYPE: PRT
<213> ORGANISM: Artificial Sequence
<220> FEATURE:
<223> OTHER INFORMATION: Synthetic Construct

<400> SEQUENCE: 6

```
Ala Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
                20                  25                  30

Ala Ala Ala Lys Asp Gly Thr Leu His Ala Arg Pro Val Val Ser Trp
            35                  40                  45

Phe Asp Gln Gly Thr Arg Asp Val Ile Gly Leu Arg Ile Ala Gly Gly
        50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
```

```
            130                 135                 140
Arg Ala Arg Thr Phe Gly Leu Glu Val Glu Glu Leu His Ser Leu Val
145                 150                 155                 160

Ala Glu Gly Val Val Val His Asn
                165

<210> SEQ ID NO 7
<211> LENGTH: 168
<212> TYPE: PRT
<213> ORGANISM: Artificial Sequence
<220> FEATURE:
<223> OTHER INFORMATION: Synthetic Construct

<400> SEQUENCE: 7

Ala Leu Ala Glu Gly Thr Arg Ile Phe Asp Pro Val Thr Gly Thr Thr
1               5                  10                  15

His Arg Ile Glu Asp Val Val Asp Gly Arg Lys Pro Ile His Val Val
                20                  25                  30

Ala Ala Ala Lys Asp Gly Thr Leu His Ala Arg Pro Val Val Ser Trp
            35                  40                  45

Phe Asp Gln Gly Thr Arg Asp Val Ile Gly Leu Arg Ile Ala Gly Gly
    50                  55                  60

Ala Ile Leu Trp Ala Thr Pro Asp Tyr Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Val Leu Val
145                 150                 155                 160

Ala Glu Gly Val Val Val His Asn
                165

<210> SEQ ID NO 8
<211> LENGTH: 168
<212> TYPE: PRT
<213> ORGANISM: Artificial Sequence
<220> FEATURE:
<223> OTHER INFORMATION: Synthetic Construct

<400> SEQUENCE: 8

Ala Leu Ala Glu Gly Thr Arg Ile Phe Asp Pro Val Thr Gly Thr Thr
1               5                  10                  15

His Arg Ile Glu Asp Val Val Asp Gly Arg Lys Pro Ile His Val Val
                20                  25                  30

Ala Ala Ala Lys Asp Gly Thr Leu His Ala Arg Pro Val Val Ser Trp
            35                  40                  45

Phe Asp Gln Gly Thr Arg Asp Val Ile Gly Leu Arg Ile Ala Gly Gly
    50                  55                  60

Ala Ile Leu Trp Ala Thr Pro Asp Val Lys Val Leu Thr Glu Tyr Gly
65                  70                  75                  80

Trp Arg Ala Ala Gly Glu Leu Arg Lys Gly Asp Arg Val Ala Gln Pro
                85                  90                  95
```

```
Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Gly Leu His Ser Leu Val
145                 150                 155                 160

Ala Glu Gly Val Val Val His Asn
                165

<210> SEQ ID NO 9
<211> LENGTH: 168
<212> TYPE: PRT
<213> ORGANISM: Artificial Sequence
<220> FEATURE:
<223> OTHER INFORMATION: Synthetic Construct

<400> SEQUENCE: 9

Ala Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp Val Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Gly Leu His Cys Leu Val
145                 150                 155                 160

Ala Glu Gly Val Val Val His Asn
                165

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Pro Thr Pro Pro Thr Pro Thr Pro Thr Pro Thr Pro Thr Pro Thr Pro
1               5                   10                  15

Pro

<210> SEQ ID NO 11
<211> LENGTH: 504
<212> TYPE: DNA
<213> ORGANISM: Artificial Sequence
<220> FEATURE:
```

<223> OTHER INFORMATION: Synthetic Construct

<400> SEQUENCE: 11

| | | | | | |
|---|---|---|---|---|---|
| gcgctggctg | aaggcacgcg | cattttttgat | ccggtcacgg | gcacgacgca | ccgcattgaa | 60
| gatgttgttg | atggccgcaa | gccgattcat | gtggttgcgg | ccgcaaaaga | tggcaccctg | 120
| cacgcccgtc | cggtcgtgag | ttggtttgat | cagggtacgc | gtgacgtcat | tggtctgcgt | 180
| atcgcgggcg | gtgcaattct | gtgggcaacc | ccggattata | aagtgctgac | ggaatatggc | 240
| tggcgtgctg | cgggtgaact | gcgtaagggt | gaccgtgttg | cacagccgcg | tcgctttgat | 300
| ggcttcggtg | acagcgcacc | gattccggct | cgcgttcaag | ccctggcaga | tgctctggat | 360
| gacaagttcc | tgcacgacat | gctggcggaa | gaactgcgtt | actctgttat | ccgcgaagtc | 420
| ctgccgaccc | gtcgcgcccg | cacgtttggt | ctggaagtgg | aagaactgca | taccctggtt | 480
| gcggaaggcg | ttgtggttca | taac | | | 504

<210> SEQ ID NO 12
<211> LENGTH: 504
<212> TYPE: DNA
<213> ORGANISM: Artificial Sequence
<220> FEATURE:
<223> OTHER INFORMATION: Synthetic Construct

<400> SEQUENCE: 12

| | | | | | |
|---|---|---|---|---|---|
| gcgctggctg | aaggcacgcg | cattttttgat | ccggtcacgg | gcacgacgca | ccgcattgaa | 60
| gatgttgttg | atggccgcaa | gccgattcat | gtggttgcgg | ccgcaaaaga | tggcaccctg | 120
| cacgcccgtc | cggtcgtgag | ttggtttgat | cagggtacgc | gtgacgtcat | tggtctgcgt | 180
| atcgcgggcg | gtgcaattct | gtgggcaacc | ccggatgtga | aagtgctgac | ggaatatggc | 240
| tggcgtgctg | cgggtgaact | gcgtaagggt | gaccgtgttg | cacagccgcg | tcgctttgat | 300
| ggcttcggtg | acagcgcacc | gattccggct | cgcgttcaag | ccctggcaga | tgctctggat | 360
| gacaagttcc | tgcacgacat | gctggcggaa | gaactgcgtt | actctgttat | ccgcgaagtc | 420
| ctgccgaccc | gtcgcgcccg | cacgtttggt | ctggaagtgg | aagaactgca | taccctggtt | 480
| gcggaaggcg | ttgtggttca | taac | | | 504

<210> SEQ ID NO 13
<211> LENGTH: 504
<212> TYPE: DNA
<213> ORGANISM: Artificial Sequence
<220> FEATURE:
<223> OTHER INFORMATION: Synthetic Construct

<400> SEQUENCE: 13

| | | | | | |
|---|---|---|---|---|---|
| gcgctggctg | aaggcacgcg | cattttttgat | ccggtcacgg | gcacgacgca | ccgcattgaa | 60
| gatgttgttg | atggccgcaa | gccgattcat | gtggttgcgg | ccgcaaaaga | tggcaccctg | 120
| cacgcccgtc | cggtcgtgag | ttggtttgat | cagggtacgc | gtgacgtcat | tggtctgcgt | 180
| atcgcgggcg | gtgcaattct | gtgggcaacc | ccggatcata | atgtgctgac | ggaatatggc | 240
| tggcgtgctg | cgggtgaact | gcgtaagggt | gaccgtgttg | cacagccgcg | tcgctttgat | 300
| ggcttcggtg | acagcgcacc | gattccggct | cgcgttcaag | ccctggcaga | tgctctggat | 360
| gacaagttcc | tgcacgacat | gctggcggaa | gaactgcgtt | actctgttat | ccgcgaagtc | 420
| ctgccgaccc | gtcgcgcccg | cacgtttggt | ctggaagtgg | aagaactgca | taccctggtt | 480
| gcggaaggcg | ttgtggttca | taac | | | 504

```
<210> SEQ ID NO 14
<211> LENGTH: 504
<212> TYPE: DNA
<213> ORGANISM: Artificial Sequence
<220> FEATURE:
<223> OTHER INFORMATION: Synthetic Construct

<400> SEQUENCE: 14
gcgctggctg aaggcacgcg catttttgat ccggtcacgg gcacgacgca ccgcattgaa      60
gatgttgttg atggccgcaa gccgattcat gtggttgcgg ccgcaaaaga tggcaccctg     120
cacgcccgtc cggtcgtgag ttggtttgat cagggtacgc gtgacgtcat tggtctgcgt     180
atcgcgggcg gtgcaattct gtgggcaacc ccggatcata agtgctgac ggaatatggc      240 tggcgtgctg cgggtgaact gcgtaagggt gaccgtgttg cacagccgcg tcgctttgat     300
ggcttcggtg acagcgcacc gattccggct cgcgttcaag ccctggcaga tgctctggat     360
gacaagttcc tgcacgacat gctggcggaa gaactgcgtt actctgttat ccgcgaagtc     420
ctgccgaccc gtcgcgcccg cacgtttggt ctggaagtga gtgaactgca taccctggtt     480
gcggaaggcg ttgtggttca taac                                            504

<210> SEQ ID NO 15
<211> LENGTH: 504
<212> TYPE: DNA
<213> ORGANISM: Artificial Sequence
<220> FEATURE:
<223> OTHER INFORMATION: Synthetic Construct

<400> SEQUENCE: 15
gcgctggctg aaggcacgcg catttttgat ccggtcacgg gcacgacgca ccgcattgaa      60
gatgttgttg atggccgcaa gccgattcat gtggttgcgg ccgcaaaaga tggcaccctg     120
cacgcccgtc cggtcgtgag ttggtttgat cagggtacgc gtgacgtcat tggtctgcgt     180
atcgcgggcg gtgcaattct gtgggcaacc ccggatcata agtgctgac ggaatatggc      240 tggcgtgctg cgggtgaact gcgtaagggt gaccgtgttg cacagccgcg tcgctttgat     300
ggcttcggtg acagcgcacc gattccggct cgcgttcaag ccctggcaga tgctctggat     360
gacaagttcc tgcacgacat gctggcggaa gaactgcgtt actctgttat ccgcgaagtc     420
ctgccgaccc gtcgcgcccg cacgtttggt ctggaagtgg aagaactgca ttctctggtt     480
gcggaaggcg ttgtggttca taac                                            504

<210> SEQ ID NO 16
<211> LENGTH: 504
<212> TYPE: DNA
<213> ORGANISM: Artificial Sequence
<220> FEATURE:
<223> OTHER INFORMATION: Synthetic Construct

<400> SEQUENCE: 16
gcgctggctg aaggcacgcg catttttgat ccggtcacgg gcacgacgca ccgcattgaa      60
gatgttgttg atggccgcaa gccgattcat gtggttgcgg ccgcaaaaga tggcaccctg     120
cacgcccgtc cggtcgtgag ttggtttgat cagggtacgc gtgacgtcat tggtctgcgt     180
atcgcgggcg gtgcaattct gtgggcaacc ccggattata agtgctgac ggaatatggc      240 tggcgtgctg cgggtgaact gcgtaagggt gaccgtgttg cacagccgcg tcgctttgat     300
ggcttcggtg acagcgcacc gattccggct cgcgttcaag ccctggcaga tgctctggat     360
gacaagttcc tgcacgacat gctggcggaa gaactgcgtt actctgttat ccgcgaagtc     420
```

```
ctgccgaccc gtcgcgcccg cacgtttggt ctggaagtgg aagaactgca tgttctggtt    480
gcggaaggcg ttgtggttca taac                                           504
```

<210> SEQ ID NO 17
<211> LENGTH: 504
<212> TYPE: DNA
<213> ORGANISM: Artificial Sequence
<220> FEATURE:
<223> OTHER INFORMATION: Synthetic Construct

<400> SEQUENCE: 17

```
gcgctggctg aaggcacgcg cattttgat ccggtcacgg gcacgacgca ccgcattgaa    60
gatgttgttg atggccgcaa gccgattcat gtggttgcgg ccgcaaaaga tggcaccctg    120
cacgcccgtc cggtcgtgag ttggtttgat cagggtacgc gtgacgtcat tggtctgcgt    180
atcgcgggcg gtgcaattct gtgggcaacc ccggatgtta aagtgctgac ggaatatggc    240
tggcgtgctg cgggtgaact gcgtaagggt gaccgtgttg cacagccgcg tcgctttgat    300
ggcttcggtg acagcgcacc gattccggct cgcgttcaag ccctggcaga tgctctggat    360
gacaagttcc tgcacgacat gctggcggaa gaactgcgtt actctgttat ccgcgaagtc    420
ctgccgaccc gtcgcgcccg cacgtttggt ctggaagtgg aagaactgca tagtctggtt    480
gcggaaggcg ttgtggttca taac                                           504
```

<210> SEQ ID NO 18
<211> LENGTH: 504
<212> TYPE: DNA
<213> ORGANISM: Artificial Sequence
<220> FEATURE:
<223> OTHER INFORMATION: Synthetic Construct

<400> SEQUENCE: 18

```
gcgctggctg aaggcacgcg cattttgat ccggtcacgg gcacgacgca ccgcattgaa    60
gatgttgttg atggccgcaa gccgattcat gtggttgcgg ccgcaaaaga tggcaccctg    120
cacgcccgtc cggtcgtgag ttggtttgat cagggtacgc gtgacgtcat tggtctgcgt    180
atcgcgggcg gtgcaattct gtgggcaacc ccggatgtta aagtgctgac ggaatatggc    240
tggcgtgctg cgggtgaact gcgtaagggt gaccgtgttg cacagccgcg tcgctttgat    300
ggcttcggtg acagcgcacc gattccggct cgcgttcaag ccctggcaga tgctctggat    360
gacaagttcc tgcacgacat gctggcggaa gaactgcgtt actctgttat ccgcgaagtc    420
ctgccgaccc gtcgcgcccg cacgtttggt ctggaagtgg aagaactgca ttgtctggtt    480
gcggaaggcg ttgtggttca taac                                           504
```

<210> SEQ ID NO 19
<211> LENGTH: 34
<212> TYPE: DNA
<213> ORGANISM: Artificial Sequence
<220> FEATURE:
<223> OTHER INFORMATION: Synthetic Construct

<400> SEQUENCE: 19

```
ccggaattcg cgctggctga aggcacgcgc attt                                34
```

<210> SEQ ID NO 20
<211> LENGTH: 39
<212> TYPE: DNA
<213> ORGANISM: Artificial Sequence
<220> FEATURE:
<223> OTHER INFORMATION: Synthetic Construct

<400> SEQUENCE: 20
cccaagcttg ttatgaacca caacgccttc cgcaaccag                                   39

<210> SEQ ID NO 21
<211> LENGTH: 39
<212> TYPE: DNA
<213> ORGANISM: Artificial Sequence
<220> FEATURE:
<223> OTHER INFORMATION: Synthetic Construct

<400> SEQUENCE: 21
cccaagcttg gcatgaacca caacgccttc cgcaaccag                                   39

<210> SEQ ID NO 22
<211> LENGTH: 75
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (58)..(58)
<223> OTHER INFORMATION: m is a or c
<220> FEATURE:
<221> NAME/KEY: misc_feature
<222> LOCATION: (59)..(60)
<223> OTHER INFORMATION: n is a, c, g, or t

<400> SEQUENCE: 22
cccaagcttg ttatgaacca caacgccttc cgcaaccagg gtatgcagtt cttccacmnn           60
cagaccaaac gtgcg                                                            75

<210> SEQ ID NO 23
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (52)..(52)
<223> OTHER INFORMATION: m is a or c
<220> FEATURE:
<221> NAME/KEY: misc_feature
<222> LOCATION: (53)..(54)
<223> OTHER INFORMATION: n is a, c, g, or t

<400> SEQUENCE: 23
cccaagcttg ttatgaacca caacgccttc cgcaaccagg gtatgcagtt cmnncacttc           60
cagacc                                                                      66

<210> SEQ ID NO 24
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (49)..(49)
<223> OTHER INFORMATION: m is a or c
<220> FEATURE:
<221> NAME/KEY: misc_feature
<222> LOCATION: (50)..(51)
<223> OTHER INFORMATION: n is a, c, g, or t

<400> SEQUENCE: 24
cccaagcttg ttatgaacca caacgccttc cgcaaccagg gtatgcagmn nttccacttc    60
cagacc    66

<210> SEQ ID NO 25
<211> LENGTH: 56
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (40)..(40)
<223> OTHER INFORMATION: m is a or c
<220> FEATURE:
<221> NAME/KEY: misc_feature
<222> LOCATION: (41)..(42)
<223> OTHER INFORMATION: n is a, c, g, or t

<400> SEQUENCE: 25
cccaagcttg ttatgaacca caacgccttc cgcaaccagm nnatgcagtt cttcca    56

<210> SEQ ID NO 26
<211> LENGTH: 35
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (16)..(16)
<223> OTHER INFORMATION: k is g or t

<400> SEQUENCE: 26
ggcaaccccg gatnnkaaag tgctgacgga atatg    35

<210> SEQ ID NO 27
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: m is a or c
<220> FEATURE:
<221> NAME/KEY: misc_feature
<222> LOCATION: (16)..(17)
<223> OTHER INFORMATION: n is a, c, g, or t

<400> SEQUENCE: 27
tccgtcagca ctttmnnatc cggggttgcc cacagaattg cac    43

<210> SEQ ID NO 28
<211> LENGTH: 44
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: k is g or t

<400> SEQUENCE: 28
ggcaaccccg gatcatnnkg tgctgacgga atatggctgg cgtg           44

<210> SEQ ID NO 29
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: m is a or c
<220> FEATURE:
<221> NAME/KEY: misc_feature
<222> LOCATION: (16)..(17)
<223> OTHER INFORMATION: n is a, c, g, or t

<400> SEQUENCE: 29
tattccgtca gcacmnnatg atccggggtt gcccacagaa ttg           43

<210> SEQ ID NO 30
<211> LENGTH: 39
<212> TYPE: DNA
<213> ORGANISM: Artificial Sequence
<220> FEATURE:
<223> OTHER INFORMATION: Synthetic Construct

<400> SEQUENCE: 30
cccaagcttg ttatgaacca caacgccttc cgcaaccag               39

<210> SEQ ID NO 31
<211> LENGTH: 37
<212> TYPE: DNA
<213> ORGANISM: Artificial Sequence
<220> FEATURE:
<223> OTHER INFORMATION: Synthetic Construct

<400> SEQUENCE: 31
ttgtggttca taaccaccat caccatcacc accccac                 37

<210> SEQ ID NO 32
<211> LENGTH: 39
<212> TYPE: DNA
<213> ORGANISM: Artificial Sequence
<220> FEATURE:
<223> OTHER INFORMATION: Synthetic Construct

<400> SEQUENCE: 32
gatggtgatg gtggttatga accacaacgc cttccgcaa               39

<210> SEQ ID NO 33
<211> LENGTH: 37
<212> TYPE: DNA
<213> ORGANISM: Artificial Sequence
<220> FEATURE:
<223> OTHER INFORMATION: Synthetic Construct

<400> SEQUENCE: 33
ttgtggttca tgcccaccat caccatcacc accccac                 37

<210> SEQ ID NO 34
<211> LENGTH: 41
<212> TYPE: DNA
<213> ORGANISM: Artificial Sequence
<220> FEATURE:

<223> OTHER INFORMATION: Synthetic Construct

<400> SEQUENCE: 34
gtgatggtga tggtgggcat gaaccacaac gccttccgca a     41

<210> SEQ ID NO 35
<211> LENGTH: 40
<212> TYPE: DNA
<213> ORGANISM: Artificial Sequence
<220> FEATURE:
<223> OTHER INFORMATION: Synthetic Construct

<400> SEQUENCE: 35
agtctactcg agtcaattcg tattctggcc cccgccgttc     40

<210> SEQ ID NO 36
<211> LENGTH: 37
<212> TYPE: DNA
<213> ORGANISM: Artificial Sequence
<220> FEATURE:
<223> OTHER INFORMATION: Synthetic Construct

<400> SEQUENCE: 36
gttgtggttc ataaccatgc agaaggcacc tttacca     37

<210> SEQ ID NO 37
<211> LENGTH: 42
<212> TYPE: DNA
<213> ORGANISM: Artificial Sequence
<220> FEATURE:
<223> OTHER INFORMATION: Synthetic Construct

<400> SEQUENCE: 37
gtgccttctg catggtttatg aaccacaacg ccttccgcaa cc     42

<210> SEQ ID NO 38
<211> LENGTH: 39
<212> TYPE: DNA
<213> ORGANISM: Artificial Sequence
<220> FEATURE:
<223> OTHER INFORMATION: Synthetic Construct

<400> SEQUENCE: 38
gcgttgtggt tcatgcccat gcagaaggca cctttacca     39

<210> SEQ ID NO 39
<211> LENGTH: 42
<212> TYPE: DNA
<213> ORGANISM: Artificial Sequence
<220> FEATURE:
<223> OTHER INFORMATION: Synthetic Construct

<400> SEQUENCE: 39
gtgccttctg catgggcatg aaccacaacg ccttccgcaa cc     42

<210> SEQ ID NO 40
<211> LENGTH: 35
<212> TYPE: DNA
<213> ORGANISM: Artificial Sequence
<220> FEATURE:
<223> OTHER INFORMATION: Synthetic Construct

<400> SEQUENCE: 40
atctgactcg agtcaaccac gacctttaac cagcc     35

```
<210> SEQ ID NO 41
<211> LENGTH: 27
<212> TYPE: DNA
<213> ORGANISM: Artificial Sequence
<220> FEATURE:
<223> OTHER INFORMATION: Synthetic Construct

<400> SEQUENCE: 41
ccggaattcg cgctggctga aggcacg                                               27

<210> SEQ ID NO 42
<211> LENGTH: 35
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (15)..(15)
<223> OTHER INFORMATION: d is a, t or g

<400> SEQUENCE: 42
ggcaaccccg gatndtaaag tgctgacgga atatg                                      35

<210> SEQ ID NO 43
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: h is a, t, or c
<220> FEATURE:
<221> NAME/KEY: misc_feature
<222> LOCATION: (17)..(17)
<223> OTHER INFORMATION: n is a, c, g, or t

<400> SEQUENCE: 43
tccgtcagca ctttahnatc cggggttgcc cacagaattg cac                             43

<210> SEQ ID NO 44
<211> LENGTH: 62
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (41)..(41)
<223> OTHER INFORMATION: h is a, t, or c
<220> FEATURE:
<221> NAME/KEY: misc_feature
<222> LOCATION: (42)..(42)
<223> OTHER INFORMATION: n is a, c, g, or t

<400> SEQUENCE: 44
cccaagcttg ttatgaacca caacgccttc cgcaaccaga hnatgcagtt cttccacttc           60
ca                                                                          62

<210> SEQ ID NO 45
<211> LENGTH: 18
<212> TYPE: PRT
<213> ORGANISM: Artificial Sequence
<220> FEATURE:
```

<223> OTHER INFORMATION: Synthetic Construct

<400> SEQUENCE: 45

Asp Trp Leu Lys Ala Phe Tyr Asp Lys Val Ala Glu Lys Leu Lys Glu
1               5                   10                  15

Ala Phe

<210> SEQ ID NO 46
<211> LENGTH: 16
<212> TYPE: PRT
<213> ORGANISM: Artificial Sequence
<220> FEATURE:
<223> OTHER INFORMATION: Synthetic Construct

<400> SEQUENCE: 46

Leu Glu Leu Glu Leu Lys Leu Lys Leu Glu Leu Glu Leu Lys Leu Lys
1               5                   10                  15

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

<400> SEQUENCE: 47

Leu Leu Leu Leu Leu Leu Lys Asp
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Phe Glu Phe Arg Phe Glu Phe Arg
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Phe Glu Phe Lys Phe Glu Phe Lys
1               5

<210> SEQ ID NO 50
<211> LENGTH: 191
<212> TYPE: PRT
<213> ORGANISM: Artificial Sequence
<220> FEATURE:
<223> OTHER INFORMATION: Synthetic Construct

<400> SEQUENCE: 50

His His His His His His Pro Thr Pro Met Ala Glu His Asn Pro Val
1               5                   10                  15

Val Met Val His Gly Ile Gly Gly Ala Ser Phe Asn Phe Ala Gly Ile
                20                  25                  30

Lys Ser Tyr Leu Val Ser Gln Gly Trp Ser Arg Asp Lys Leu Tyr Ala
            35                  40                  45

```
Val Asp Phe Trp Asp Lys Thr Gly Thr Asn Tyr Asn Gly Pro Val
        50                  55                  60

Leu Ser Arg Phe Val Gln Lys Val Leu Asp Glu Thr Gly Ala Lys Lys
 65              70                  75                  80

Val Asp Ile Val Ala His Ser Met Gly Gly Ala Asn Thr Leu Tyr Tyr
                85                  90                  95

Ile Lys Asn Leu Asp Gly Gly Asn Lys Val Ala Asn Val Val Thr Leu
            100                 105                 110

Gly Gly Ala Asn Arg Leu Thr Thr Gly Lys Ala Leu Pro Gly Thr Asp
            115                 120                 125

Pro Asn Gln Lys Ile Leu Tyr Thr Ser Ile Tyr Ser Ser Ala Asp Met
        130                 135                 140

Ile Val Met Asn Tyr Leu Ser Arg Leu Asp Gly Ala Arg Asn Val Gln
145                 150                 155                 160

Ile His Gly Val Gly His Ile Gly Leu Leu Tyr Ser Ser Gln Val Asn
                165                 170                 175

Ser Leu Ile Lys Glu Gly Leu Asn Gly Gly Gln Asn Thr Asn
            180                 185                 190

<210> SEQ ID NO 51
<211> LENGTH: 31
<212> TYPE: PRT
<213> ORGANISM: Artificial Sequence
<220> FEATURE:
<223> OTHER INFORMATION: Synthetic Construct

<400> SEQUENCE: 51

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
                20                  25                  30

<210> SEQ ID NO 52
<211> LENGTH: 573
<212> TYPE: DNA
<213> ORGANISM: Artificial Sequence
<220> FEATURE:
<223> OTHER INFORMATION: Synthetic Construct

<400> SEQUENCE: 52
caccatcacc atcaccaccc caccccctatg gctgaacaca atccagtcgt tatggttcac      60
ggtattggag gggcatcatt caattttgcg ggaattaaga gctatctcgt atctcagggc     120
tggtcgcggg acaagctgta tgcagttgat ttttgggaca agacaggcac aaattataac     180
aatggaccgg tattatcacg atttgtgcaa aaggttttag atgaaacggg tgcgaaaaaa     240
gtggatattg tcgctcacag catgggggc gcgaacacac tttactacat aaaaaatctg     300
gacggcggaa ataaagttgc aaacgtcgtg acgcttggcg gcgcgaaccg tttgacgaca     360
ggcaaggcgc ttccgggaac agatccaaat caaaagattt tatacacatc catttacagc     420
agtgccgata tgattgtcat gaattactta tcaagattag atggtgctag aaacgttcaa     480
atccatggcg ttggacacat cggccttctg tacagcagcc aagtcaacag cctgattaaa     540
gaagggctga acggcggggg ccagaatacg aat                                    573

<210> SEQ ID NO 53
<211> LENGTH: 93
<212> TYPE: DNA
<213> ORGANISM: Artificial Sequence
```

```
<220> FEATURE:
<223> OTHER INFORMATION: Synthetic Construct

<400> SEQUENCE: 53
catgcagaag gcacctttac cagcgatgtt agcagctatc tggaaggtca ggcagcaaaa      60
gaatttattg catggctggt taaaggtcgt ggt                                  93
```

FUSION PROTEINS COMPRISING A MTU ΔI-CM INTEIN VARIANT AND METHODS OF PROTEIN PURIFICATION

CROSS-REFERENCE TO RELATED APPLICATIONS

This application is a continuation of International Application No. PCT/CN2018/122075, filed Dec. 19, 2018, which is hereby incorporated by reference in its entirety.

TECHNICAL FIELD

The invention relates to the field of bioengineering. More specifically, the present invention relates to a Mtu ΔI-CM intein variant or a biologically active fragment thereof, and a method for producing and purifying a molecule of interest using the same.

BACKGROUND

Intein is a self-splicing protein, which exists in the protein of some specific hosts. Intein is able to remove itself from a precursor protein by self-splicing reaction, and allows exteins at the two flanking regions to be connected through a peptide bond to become a mature protein having biological activity.

One of the main uses of intein is to be combined with purification tags for protein purification. By mutating an active amino acid at one terminus of a self-splicing intein into alanine, the activity of the terminus can be silenced, or through appropriate evolution and modification, an intein cleaved only at the N-terminus or C-terminus can be obtained, which can be used in purification methods based on purification tags. Generally, N-terminal cleavage of intein is induced by a thiol reagent, while C-terminal cleavage can be induced by a pH shift or a thiol reagent. Compared with thiol reagent-induced cleavage of intein, pH-induced cleavage has three major characteristics: (1) the pH-induced cleavage belongs to C-terminal cleavage, which can generate an authentic N-terminus of a molecule of interest, which is especially important for the production of pharmaceutical polypeptides; (2) no reducing agent is needed, which is beneficial to the production of polypeptides and proteins with disulfide bonds; and (3) economical and convenient, because only the pH value of a buffer solution is needed to be changed. It is estimated that a buffer solution for thiol reagent-induced cleavage is as expensive as cheap proteases (e.g., Pre-Scission protease of GE or TagZyme protease of Qiagen). However, the price of a buffer solution for pH-induced cleavage can be two orders of magnitude lower than that of the thiol reagent buffer solution or cheap enzymes, and thus pH-induced cleavage is of great application potentials. However, when using a pH-induced C-terminal cleavage intein (e.g., Mtu ΔI-CM intein), a significant premature cleavage will occur during the expression of fusion proteins in recombinant hosts. Therefore, the development of more controllable pH-induced inteins will greatly benefit the application of protein purification methods based on purification tags.

SUMMARY OF THE INVENTION

The present invention provides a Mtu ΔI-CM intein variant containing one or more mutations or a biologically active fragment thereof, and a method for producing and purifying a molecule of interest using the same. The specific technical embodiments are described as follows:

In a first aspect, the present invention is directed to an isolated polypeptide comprising a variant of a Mtu ΔI-CM intein or a biologically active fragment thereof, the Mtu ΔI-CM intein having an amino acid sequence set forth in SEQ ID NO:1, wherein the polypeptide comprises one or more amino acid substitutions at one or more sites corresponding to one or more sites within the range of 5 Å around H157 and H167 of the Mtu ΔI-CM intein, and the N-terminal cleavage activity of the polypeptide remains silenced; and comparing with the Mtu ΔI-CM intein having an amino acid sequence set forth in SEQ ID NO:1, the amino acid substitutions enable the polypeptide to have reduced C-terminal cleavage efficiency at a first pH value and similar or increased C-terminal cleavage efficiency at a second pH value.

In a second aspect, the present invention is directed to an isolated fusion protein comprising the polypeptide of the first aspect, a purification tag and a molecule of interest, wherein the purification tag is located at the N terminus of the polypeptide and the molecule of interest is located at the C terminus of the polypeptide.

In a third aspect, the present invention is directed to an isolated polynucleotide comprising a nucleotide sequence encoding the polypeptide of the first aspect.

In a fourth aspect, the present invention is further directed to an isolated polynucleotide comprising a nucleotide sequence encoding the fusion protein of the second aspect.

In a fifth aspect, the present invention is directed to a recombinant vector comprising the isolated polynucleotide of the third or fourth aspect.

In a sixth aspect, the present invention is directed to a host cell comprising the polynucleotide of the third or fourth aspect or the recombinant vector of the fifth aspect.

In another aspect, the present invention is directed to a method for producing a molecule of interest, and the method comprises the steps of: (a) cultivating host cells comprising the polynucleotide of the fourth aspect to express the fusion protein; (b) disrupting the host cells and recovering the fusion protein produced in step (a) at a first pH value; (c) cleaving the fusion protein at a second pH value to release the molecule of interest; and (d) recovering the molecule of interest.

In another aspect, the present invention is directed to a method for purifying a molecule of interest from a sample, comprising the steps of: (a) providing a sample containing the fusion protein of the second aspect; (b) collecting the fusion protein by a purification tag; (c) adjusting pH value such that the molecule of interest is cleaved from the fusion protein; and (d) recovering the molecule of interest.

In another aspect, the present invention relates to a method for screening a polypeptide for producing or purifying a molecule of interest, and the method comprises the following steps: (a) preparing a fusion protein comprising a variant of a Mtu ΔI-CM intein set forth in SEQ ID NO:1 or a biologically active fragment of the variant, and the molecule of interest attached to the C terminus thereof; and (b) under the condition that the fusion protein has activity, screening to select the variant or biologically active fragment of the variant having reduced C-terminal cleavage efficiency at a first pH value and similar or increased C-terminal cleavage efficiency at a second pH value as compared with the Mtu ΔI-CM intein set forth in SEQ ID NO:1, wherein the N-terminal cleavage activity of the variant or biologically active fragment of the variant is silenced.

DETAILED DESCRIPTION OF THE INVENTION

Figure 1:
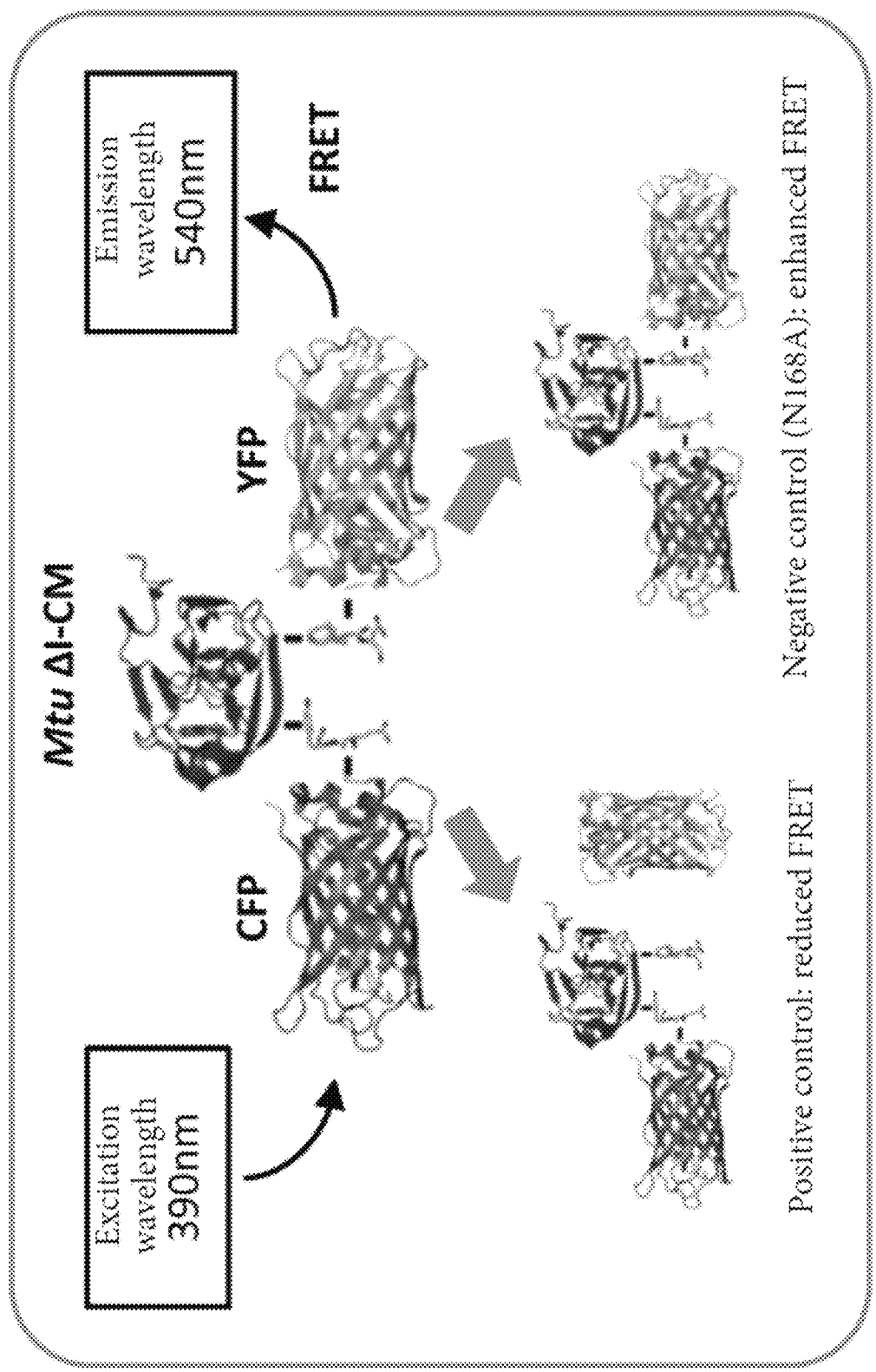
FIG. 1 is a diagram of constructing a FRET system. A positive control system C-I-Y and a negative control system C-Ia-Y are shown. It shows the cleavage products and related FRET values corresponding to a positive control and a negative control, respectively.

Mtu ΔI-CM intein is an intein modified by the Wood group (David W. Wood et al., A genetic system yields self-cleaving inteins for bioseparations, Nat Biotechnol., 17(9):889-92 (1999)), which can be rapidly cleaved at the C terminus. Firstly, Wood group deleted an endonuclease domain from a Mtu RecA maxi-intein (440aa) from *Mycobacterium tuberculosis*, leaving 110 amino acids at the N terminus and 58 amino acids at the C terminus, so that to engineer the Mtu RecA maxi-intein into a mini intein. Further, the Wood group evolved the mini intein by introducing four point mutations: C1A, blocking the N-terminal cleavage activity; V67L, restoring the stability of the intein (the intein became unstable after the deletion of the endonuclease domain); D24G, having no effect on phenotype; and D150G (corresponding to the mutation site D422G in the Mtu RecA maxi-intein), cutting off the connection between C-terminal cleavage and N-terminal cleavage to improve the C-terminal cleavage activity of the intein. The resulted variant is called Mtu ΔI-CM intein. Mtu ΔI-CM intein can be rapidly cleaved at the C terminus. As used herein, the amino acid sequence of the term "Mtu ΔI-CM intein" comprises the mutation CIA, as well as one or more mutations of V67L, D24G, and D150G (corresponding to the mutation site D422G in the Mtu RecA maxi-intein). In one embodiment of the invention, the amino acid sequence of the Mtu ΔI-CM intein comprises mutations CIA, V67L, and D150G (corresponding to the mutation site D422G in the Mtu RecA maxi-intein). In one specific embodiment of the invention, the Mtu ΔI-CM intein has an amino acid sequence set forth in SEQ ID NO:1, with a length of 168 amino acids and a molecular weight of 18.5 kDa. In one embodiment of the invention, one or more of amino acids E152, V153, E154, E155, L156, T158, L159, V166, H167, L2, H73, K74, V75, W81, H157, and V165 that within a range of 5 Å around H157 and H167 in the Mtu ΔI-CM intein are subjected to site-directed mutagenesis.

As used herein, the term "variant" refers to a polypeptide or polynucleotide comprising one or more amino acid or nucleotide mutations compared with its parent. The terms "variant" and "mutant" are used interchangeably herein. In some embodiment, the term "template" refers to a parent, i.e., Mtu ΔI-CM intein.

As used herein, the term "biologically active" entity or an entity having "biological activity" refers to an entity having reduced C-terminal cleavage efficiency compared with the Mtu ΔI-CM intein at a first pH value, but has similar or increased C-terminal cleavage efficiency compared with the Mtu ΔI-CM intein at a second pH value. As used herein, "biologically active fragment of Mtu ΔI-CM intein variant" is an active fragment exhibits similar but not necessarily the same activity as the Mtu ΔI-CM intein variant of the invention. In one embodiment, the amino acid at A1 of the Mtu ΔI-CM intein variant or the biologically active fragment of the variant does not mutate. In one embodiment, the amino acid at A1 of the Mtu ΔI-CM intein variant or the biologically active fragment of the variant does not mutate, and one or more of the amino acids at L67, G150 (corresponding to the mutation site G422 in the Mtu RecA maxi-intein) and G24 do not mutate. In a specific embodiment, the amino acids at A1, L67 and G150 of the Mtu ΔI-CM intein variant or the biologically active fragment of the variant do not mutate.

As used herein, the term "amino acid" is an organic compound containing an amino group and a carboxylic acid group. In the present invention, amino acids include 20 natural amino acids, unnatural amino acids, and amino acid analogs (i.e., amino acids in which α-carbon has a side chain). Natural amino acids include amino acids selected from the group consisting of tyrosine, glycine, phenylalanine, methionine, alanine, serine, isoleucine, leucine, threonine, valine, proline, lysine, histidine, glutamine, glutamic acid, tryptophan, arginine, aspartic acid, asparagine, and cysteine. The abbreviations of natural amino acid residues are shown below in Table 1:

TABLE 1

| Symbol | | |
| --- | --- | --- |
| 1-letter | 3-letter | amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | unknown or others |

Examples of unnatural amino acids and amino acid analogs are known to those skilled in the art, and include but not limited to 2-aminoadipic acid (Aad), 3-aminoadipic acid (Bead), β-alanine/β-amino-propionic acid (Bala), 2-aminobutyric acid (Abu), 6-aminocaproic acid (Acp), 2-aminoheptanoic acid (Ahe), 2-aminoisobutyric acid (Aib), 3-aminoisobutyric acid (Baib), 2-aminoheptanoic acid (Apm), 2,4-diaminobutyric acid (Dbu), desmosine (Des), 2,2'-diaminopimelate (Dpm), 2,3-diaminopropionic acid (Dpr), N-etHylglycine (EtGly), N-ethylasparagine (EtAsn), hydroxylysine (hyl), allo-hydroxylysine (Ahyl), 3-hydroxyproline (3Hyp), 4-hydroxyproline (4Hyp), isodesmosine (Ide), alto-isoleucine (Aile), N-methylglycine, sarcosine (MeGly), N-methylisoleucine (MeIle), 6-N-methyllysine (MeLys), N-methylvaline (MeVal), norvaline (Nva), norleucine (Nle) and ornithine (Orn).

As used herein, the term "polypeptide" refers to a biomolecule composed of amino acids linked by peptide bonds. The terms "polypeptide", "peptide" and "protein" are used interchangeably herein.

As used herein, the term "corresponding to" or "corresponds to" refers to the portions, sites or regions aligned with each other when a person skilled in the art uses a known sequence alignment method to align two or more related polypeptide or nucleic acid sequences (including the sequences of molecules, regions of molecules and/or theoretical sequences) based on maximum matching to obtain the highest level of matching. In other words, when two or more polypeptide or nucleic acid sequences are optimally matched, two similar sites (or portions or regions) are aligned. When aligning two or more sequences, similar portions/sites/regions are identified based on the sites along linear nucleic acid or amino acid sequences.

As used herein, the term "host cell" refers to a cell used to receive, maintain, replicate and amplify a vector. Host cells are particularly used for expressing the fusion polypeptide of the present invention encoded by a vector. Host cells can be used in the present invention include, but not limited to, cells are of prokaryotes and eukaryotes origin. In one embodiment, prokaryotes are bacteria selected from the group consisting of *Escherichia, Mycobacterium* (e.g., *Mycobecterium Tuberculosis*), *Bacillus, Salmonella, Pseudomonas* and *Streptomyces*. In a preferred embodiment, the host cells are *Escherichia* cells, more preferably *Escherichia coli* cells. In a specific embodiment of the present invention, the host cells used herein are *Escherichia coli* BL21 (DE3) strain cells. In one embodiment, the eukaryotes are selected from *Pichia*.

Therefore, in a first aspect, the present invention relates to an isolated polypeptide comprising a variant of Mtu ΔI-CM intein or a biologically active fragment thereof, the Mtu ΔI-CM intein having an amino acid sequence set forth in SEQ ID NO:1, wherein the polypeptide comprises amino acid substitutions at sites corresponding to sites within the range of 5 Å around H157 and H167 of the Mtu ΔI-CM intein, and the N-terminal cleavage activity of the polypeptide remains silenced; and compared with the Mtu ΔI-CM intein set forth in SEQ ID NO:1, the amino acid substitutions enable the polypeptide having reduced C-terminal cleavage efficiency at a first pH value and similar or increased C-terminal cleavage efficiency at a second pH value. As used herein, "the reduced cleavage efficiency" refers to cleavage efficiency reduced from 87% of the Mtu ΔI-CM intein to 18%-45%, preferably lower than 35%, under the same conditions; and "the similar or increased cleavage efficiency" refers to cleavage efficiency changing from 85% of the Mtu ΔI-CM intein to 71%-92%, preferably higher than 80%, under the same conditions.

In one embodiment, the first pH value is neutral to weakly basic. In a particular embodiment, the first pH value is a pH value within the host cell or is close to the pH value within the host cell. In a specific embodiment, the first pH value is 7.2-8.5. In a preferred embodiment, the first pH value is 7.4-7.8. In a more preferred embodiment, the first pH value is 7.4-7.6. In the most preferred embodiment, the first pH value is 7.5. In one embodiment, the second pH value refers to a pH value which is weakly acidic. In a preferred embodiment, the second pH value is 5.5-6.8, and preferably 5.5-6.5. In the most preferred embodiment, the second pH value is 6.0.

In one embodiment, the amino acid substitutions comprise substitutions at one or more of the sites E152, V153, E154, E155, L156, T158, L159, V166, H167, L2, H73, K74, V75, W81, H157, and V165 corresponding to SEQ ID NO:1. In a preferred embodiment, the amino acid substitutions comprise substitutions at one or more of the sites H73, K74, E152, E154, E155 and T158 corresponding to SEQ ID NO:1. In a preferred embodiment, the amino acid substitutions comprise substitutions at one or more of the sites H73, K74, E154 and T158 corresponding to SEQ ID NO:1. In a more preferred embodiment, the amino acid substitutions occur at sites H73 and T158 corresponding to SEQ ID NO:1. In another embodiment, the amino acid substitutions are selected from the group consisting of H73Y, H73V; K74N; E154S; and/or T158V, T158C or T158S corresponding to SEQ ID NO:1. In a specific embodiment, the amino acid substitutions are H73Y and T158V, H73V and T158S; or H73V and T158C corresponding to SEQ ID NO:1.

Methods for introducing amino acid mutations into polypeptides are well known to those skilled in the art. See, for example, Ausubel, Current Protocols in Molecular Biology, John Wiley and Sons, Inc. (1994); T. Maniatis et al., Molecular Cloning: A Laboratory Manual, Cold Spring Harbor laboratory, Cold Spring Harbor, N.Y. (1989). For example, commercially available kits such as QuikChange™ site-directed mutagenesis kit Stratagene can be used, or polypeptides with mutations can be synthesized directly by chemical methods.

Those skilled in the art understand that the polypeptide of the first aspect of the present invention can be further modified, for example, by introducing substitution, addition or deletion of one or more additional amino acids, while still maintaining the biological activity of the variant of the Mtu ΔI-CM intein or the biologically active fragment of the variant, i.e., compared with the Mtu ΔI-CM intein, the further modified polypeptide has reduced C-terminal cleavage efficiency at the first pH value, but has similar or increased C-terminal cleavage efficiency at the second pH value. As used herein, "the reduced cleavage efficiency" means that compared with the Mtu ΔI-CM intein, the cleavage efficiency of the Mtu ΔI-CM intein variant of the present invention is reduced by about 30% to about 40%, preferably by about 40% to about 50%, more preferably by about 50% to about 70%, and still more preferably by about 70% to about 80%, or more under the same first pH value. In a specific example, under the first pH value, the cleavage efficiency of the Mtu ΔI-CM intein variant of the present invention is reduced to 18%-45%, preferably less than 35%, compared to about 87% of the Mtu ΔI-CM intein. As used herein, "the similar or increased cleavage efficiency" means that compared with the Mtu ΔI-CM intein, the cleavage efficiency of the Mtu ΔI-CM intein variant of the present invention decreases by no more than about 20%, preferably by no more than about 10%, or more preferably by no more than about 5%, or remains substantially the same, or increases by about 5%, preferably by about 10%, or more preferably by about 20% or more, under the same second pH value. In a specific embodiment, under the second pH value, compared with the about 85% cleavage efficiency of the Mtu ΔI-CM intein, the cleavage efficiency of the Mtu ΔI-CM intein variant of the present invention is 71%-92%, preferably more than 80%.

In one embodiment, the polypeptide may be subjected to conservative amino acid substitutions. As used herein, the term "conservative amino acid substitution" refers to the substitution of one amino acid residue by another amino acid residue of which a side chain R group having similar chemical properties, such as charge or hydrophobicity. Generally speaking, conservative amino acid substitutions do not substantially change the functional properties of proteins.

Examples of amino acid groups having side chains with similar chemical properties include: (1) aliphatic side chains: glycine, alanine, valine, leucine and isoleucine; (2) aliphatic hydroxyl side chains: serine and threonine; (3) side chains containing amides: asparagine and glutamine; (4) aromatic side chains: phenylalanine, tyrosine and tryptophan; (5) basic side chains: lysine, arginine and histidine; (6) acidic side chains: aspartic acid and glutamic acid; and (7) sulfur-containing side chains: cysteine and methionine. Preferred conservative amino acid substitutions include valine-leucine-isoleucine, phenylalanine-tyrosine, lysine-arginine, alanine-valine, glutamic acid-aspartic acid, and asparagine-glutamine. Those skilled in the art can determine whether an amino acid substitution belongs to conservative amino acid substitutions according to the teaching of the prior art. Conservative amino acid substitutions can be carried out according to Table 2 below:

TABLE 2

| Original Residue | Conservative Amino Acid Substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Herein, when used to define a polypeptide or polynucleotide sequence, the terms "comprising," "including," "having" or synonymous thereof are open-ended, meaning that other amino acids or nucleotide residues are optionally included at one or both termini of the defined polypeptide or polynucleotide sequence. As used herein, when defining a polypeptide or polynucleotide sequence, the term "consisting of" or "consists of" is closed, meaning that other amino acids or nucleotide residues are no longer contained at the two termini of the defined polypeptide or polynucleotide sequence.

In one embodiment, the polypeptide comprises the amino acid sequence of SEQ ID NO:2, SEQ ID NO:3, SEQ ID NO:4, SEQ ID NO:5, SEQ ID NO:6, SEQ ID NO:7, SEQ ID NO:8 or SEQ ID NO:9. In a preferred embodiment, the polypeptide consists of the amino acid sequence of SEQ ID NO:2, SEQ ID NO:3, SEQ ID NO:4, SEQ ID NO:5, SEQ ID NO:6, SEQ ID NO:7, SEQ ID NO:8 or SEQ ID NO:9.

As used herein, the term "sequence identity" refers to the degree to which amino acid or nucleotide sequences remain unchanged. Methods for evaluating the degree of sequence identity between amino acid sequences or nucleotide sequences are known to those skilled in the art. For example, amino acid sequence identity is usually measured by sequence analysis software. For example, the BLAST program of the NCBI database can be used to determine the identity. For the determination of sequence identity, see, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In one embodiment, the polypeptide of the first aspect has conservative amino acid substitutions. Therefore, in one embodiment, the amino acid sequence of the polypeptide of the first aspect has one or more amino acids substitutions, deletions and/or additions as compared with the amino acid sequence set forth in SEQ ID NO:2, SEQ ID NO:3, SEQ ID NO:4, SEQ ID NO:5, SEQ ID NO:6, SEQ ID NO:7, SEQ ID NO:8 or SEQ ID NO:9. In another embodiment, the polypeptide comprises an amino acid sequence having at least 85%, 86%, 87%, 88%, 89%, 90%, 91%, 92%, 93%, 94%, 95%, 96%, 97%, 98% or 99% sequence identity with any sequence set forth in SEQ ID NO:2, SEQ ID NO:3, SEQ ID NO:4, SEQ ID NO:5, SEQ ID NO:6, SEQ ID NO:7, SEQ ID NO:8 or SEQ ID NO:9. In the above embodiment, because the amino acid substitutions are conservative amino acid substitutions, the polypeptide of the present invention still maintains the biological activity of the Mtu ΔI-CM intein, and has reduced cleavage efficiency at the first pH value, but has similar or increased cleavage efficiency at the second pH value compared with the Mtu ΔI-CM intein. As used herein, "the reduced cleavage efficiency" means that compared with the Mtu ΔI-CM intein, the cleavage efficiency of the Mtu ΔI-CM intein variant of the present invention is reduced by about 30% to about 40%, preferably by about 40% to about 50%, more preferably by about 50% to about 70%, and still more preferably by about 70% to about 80%, or more under the same first pH value. In a specific embodiment, under the first pH value, compared with about 87% cleavage efficiency of the Mtu ΔI-CM intein, the cleavage efficiency of the Mtu ΔI-CM intein variant of the present invention is reduced to 18%-45%, preferably lower than 35%. As used herein, "the similar or increased cleavage efficiency" means that compared with the Mtu ΔI-CM intein, the cleavage efficiency of the Mtu ΔI-CM intein variant of the present invention decreases by no more than about 20%, preferably by no more than about 10%, or more preferably by no more than about 5%, or remains substantially the same, or increases by about 5%, preferably by about 10%, or more preferably by about 20% or more under the same second pH value. In a specific embodiment, under the second pH value, compared with the about 85% cleavage efficiency of the Mtu ΔI-CM intein, the cleavage efficiency of the Mtu ΔI-CM intein variant of the present invention is 71%-92%, and preferably more than 80%.

In a second aspect, the present invention relates to an isolated fusion protein comprising the polypeptide of the first aspect, a purification tag and a molecule of interest, wherein the purification tag is located at the N terminus of the polypeptide and the molecule of interest is located at the C terminus of the polypeptide.

As used herein, the term "purification tag" refers to a molecule that purifies a molecule of interest through its own properties. Many different types of purification tags (according to the function) have been developed, including affinity tags, aggregating tags and compound tags. Different tag types are selected according to different purification methods to be adopted. Tags are also in various forms, including short peptides, antigenic epitopes, folded protein domains and the like. These tags are expressed together with the molecule of interest, so that the molecule of interest can be selectively captured and/or purified rapidly through a certain method. For example, the affinity tags achieve the capture and/or purification by affinity resins which can specifically bind thereto. The aggregating tags have self-aggregatable property or induced aggregatable property, which achieve the capture and/or purification by centrifugation. Many tags also have other functions in addition to purification, such as promoting dissolution or making the molecule of interest easy to detect.

In a preferred embodiment, the purification tag is an affinity tag. In another preferred embodiment, the purification tag is an aggregating tag. In another specific embodiment, the aggregating tag is an amphipathic self-assembling short peptide.

As used herein, the term "self-assembling short peptide" refers to a small peptide with amphipathic (hydrophilic and hydrophobic) properties, which is composed of hydrophilic (polar) amino acids and hydrophobic (nonpolar) amino acids arranged according to a certain rule. Amphipathic peptides are divided into two categories. One category contains other organic molecules in addition to amino acid residues, such as fatty acid chains; and the other category is composed of natural amino acids only. The latter can be divided into three categories according to different secondary structures: α-helix, β-sheet and random coil. In one embodiment, the amphipathic self-assembling short peptide of the present invention is selected from: 18A (DWLKAFYDK-VAEKLKEAF) (SEQ ID NO:45), ELK16 (LELELKLKLELELKLK) (SEQ ID NO:46), $L_6KD$ (LLLLLLKD) (SEQ ID NO:47), EFR8 (FEFRFEFR) (SEQ ID NO:48) and EFK8 (FEFKFEFK) (SEQ ID NO:49). In a specific embodiment, the amphipathic self-assembling short peptide of the present invention is $L_6KD$ (LLLLLLKD) (SEQ ID NO:47).

As used herein, the term "spacer" refers to a polypeptide in a certain length consisting of amino acids with low hydrophobicity and low charge effect, which allows the connected parts to be fully expanded and fully folded into their respective natural conformations without interference when co-existed in a fusion protein. Spacers commonly used in the art include, for example, flexible GS-type linker rich in glycine (G) and serine (S), and rigid PT-type linker rich in proline (P) and threonine (T). In some embodiments, the purification tag is attached to the N terminus of the polypeptide through a spacer. In a preferred embodiment, the spacer is a PT-type linker. In some specific embodiments, the spacer comprises the sequence PTPPTTPTPPTTPTPT (SEQ ID NO:10).

In one embodiment, the molecule of interest is a peptide segment. In a preferred embodiment, the peptide segment is 20, 50, 70, 100, 150, 200, 250, 300, 350, 400, 450 or 500 amino acid residues in length, or any length in between any two lengths stated above.

In another aspect, the present invention relates to an isolated polynucleotide comprising a nucleotide sequence encoding the isolated polypeptide in the embodiments of the first aspect.

Polynucleotide sequences encoding the Mtu ΔI-CM intein can be obtained from sequence databases available in the art. For example, polynucleotide sequences encoding the Mtu RecA maxi-intein can be obtained according to the amino acid sequence of the Mtu RecA maxi-intein in the NCBI database and by introducing mutations made by the Wood group (David W. Wood et al., A genetic system yields self-cleaving inteins for bioseparations (1999)).

In one embodiment, the isolated polynucleotide of the present invention comprises the nucleotide sequence selected from a group consisting of: the nucleotide sequence set forth in SEQ ID NO:11, SEQ ID NO:12, SEQ ID NO:13, SEQ ID NO:14, SEQ ID NO:15, SEQ ID NO:16, SEQ ID NO:17 or SEQ ID NO:18. In a preferred embodiment, the isolated polynucleotide of the present invention consists of the nucleotide sequence set forth in SEQ ID NO:11, SEQ ID NO:12, SEQ ID NO:13, SEQ ID NO:14, SEQ ID NO:15, SEQ ID NO:16, SEQ ID NO:17 or SEQ ID NO:18. In one embodiment, the isolated polynucleotide of the present invention comprises a nucleotide sequence having at least 85%, 86%, 87%, 88%, 89%, 90%, 91%, 92%, 93%, 94%, 95%, 96%, 97%, 98% or 99% sequence identity comparing with the nucleotide sequence set forth in SEQ ID NO:11, SEQ ID NO:12, SEQ ID NO:13, SEQ ID NO:14, SEQ ID NO:15, SEQ ID NO:16, SEQ ID NO:17 or SEQ ID NO:18. In one embodiment, the isolated polynucleotide of the present invention comprises a polynucleotide sequence which hybridizes under stringent conditions with the nucleotide sequence set forth in SEQ ID NO:11, SEQ ID NO:12, SEQ ID NO:13, SEQ ID NO:14, SEQ ID NO:15, SEQ ID NO:16, SEQ ID NO:17 or SEQ ID NO:18. In the above embodiments, the polynucleotide of the present invention encodes the polypeptide which still retains the biological activity of the Mtu ΔI-CM intein, and compared with the Mtu ΔI-CM intein, the polypeptide has reduced cleavage efficiency at the first pH value but similar or increased cleavage efficiency at the second pH value.

As used herein, the term "hybridization under stringent conditions" refers to annealing of polynucleotide molecules and target nucleic acid molecules through complementary base pairing. Those skilled in the art are familiar with parameters affecting specific hybridization, such as the length and composition of specific molecules. Parameters particularly relevant to hybridization also include, for example, annealing and washing temperatures, buffer composition and salt concentration. In one embodiment, hybridization under stringent conditions refers to hybridization under high stringency conditions, i.e., 0.1×SSPE, 0.1% SDS, 65° C. In one embodiment, hybridization under stringent conditions refers to hybridization under moderate stringency conditions, i.e., 0.2×SSPE, 0.1% SDS, 50° C. In one embodiment, hybridization under stringent conditions refers to hybridization under low stringency conditions, i.e., 0.2× SSPE, 0.1% SDS, 40° C. Equivalent stringent conditions are known in the art. Those skilled in the art can adjust the parameters affecting hybridization to accomplish hybridization of polynucleotide molecules and target nucleic acid molecules under low, moderate or high stringency conditions.

In another aspect, the present invention also relates to an isolated polynucleotide comprising a nucleotide sequence encoding the fusion protein according to any one of the preceding embodiments.

In another aspect, the present invention also relates to a recombinant vector comprising a polynucleotide encoding the aforementioned polypeptide or fusion protein. In one embodiment, the sequence of the polynucleotide encoding the fusion protein is operably linked to an expression control sequence to perform desired transcription and ultimately produce the fusion protein. Suitable expression control sequences include, but not limited to, promoters, enhancers, ribosome interaction sites such as ribosome binding sites, polyadenylation sites, transcription splicing sequences, transcription termination sequences, sequences that stabilize mRNA, and the like.

In one embodiment, vectors used to construct the recombinant vector of the present invention include, but not limited to, vectors that autonomously replicate in host cells, such as plasmid vectors; and vectors can be integrated into host cell DNA and replicated together with the host cell DNA. In one embodiment, the vectors are commercially available vectors. In a specific embodiment, an expression vector of the present invention is derived from pET30a(+) from Novagen Inc.

In another aspect, the present invention relates to a host cell comprising the isolated polynucleotide according to any of the preceding embodiments or the recombinant vector according to any of the preceding embodiments. In one embodiment, the recombinant vector enters the host cell by transformation. In one embodiment, the host cell expresses the fusion protein of the present invention.

As used herein, the term "transformation" means that one, two or more copies of the isolated polynucleotide or recombinant vector of the present invention are transferred into the host cell. Methods for introducing exogenous polynucleotides or vectors into host cells are known to those skilled in the art, including but not limited to: microinjection (Capechi et al., 1980, Cell, 22:479), $Ca_2(PO_4)_3$ mediated transfection (Chen et al., 1987, Mol. Cell Biol., 7:2745), DEAE dextran mediated transfection, electroporation (Chu et al., 1987, Nucleic Acid Res., 15: 1311), liposome transfection/liposome fusion (Feigner et al., 1987, Proc. Natl. Acad. Sci., USA 84:7413), particle bombardment (Yang et al., 1990, Proc. Natl. Acad. Sci., USA 87:9568) and gene gun.

The term "expression" generally refers to the process of producing a polypeptide by transcription and translation of a polynucleotide. As used herein, the term "expression" can be understood as "heterologous expression", that is, expression of polypeptides encoded by heterologous nucleic acids in vivo in host cells or in vitro.

In another aspect, the present invention also provides a method for producing a molecule of interest, which comprises the following steps: cultivating a host cell comprising a polynucleotide encoding the fusion protein according to any of the preceding embodiments to express the fusion protein; disrupting the host cell and recovering insoluble precipitate at the first pH value; cleaving the insoluble precipitate at the second pH value to release the molecule of interest; and recovering the molecule of interest, wherein the insoluble precipitate is an aggregate of insoluble active fusion proteins.

In one embodiment, the first pH value refers to the pH value in the host cell or close to the pH value in the host cell, which is neutral to weakly basic. In a preferred embodiment, the first pH value is 7.2-8.5. In a preferred embodiment, the first pH value is 7.4-7.8. In the most preferred embodiment, the first pH value is 7.5. In one embodiment, the second pH value is weakly acidic. In a preferred embodiment, the second pH value is 5.5-6.8. In a preferred embodiment, the first pH value is 5.5-6.5. In the most preferred embodiment, the second pH value is 6.0.

In a specific embodiment, the host cell is cultivated under physiological conditions (e.g., normal temperature 18-37° C., neutral pH 7.4-7.8) to express the fusion protein of the present invention, and the fusion protein can directly from the insoluble precipitate in an inclusion body. Compared with protein expression in a soluble state, the formation of the insoluble precipitate can prevent the fusion protein from being degraded in the cell and thus greatly increase the stability of the fusion protein or the molecule of interest. Meanwhile, since expression is carried out in the host cell cultivated under normal physiological conditions, the extension of the cultivation period of the host cell is avoided, and the production amount and production rate of the fusion protein can be improved by adopting suitable culture conditions.

The term "disrupting the host cell" refers to the use of certain methods to lyse the host cell and release substances in cytoplasm. Methods for disrupting the host cell which can be used in the present invention include, but not limited to the following treatments: ultrasonication, homogenizing, high-pressure (e.g., in a French press), osmolysis, detergent, lyase, organic solvent, or combinations thereof. In one embodiment, the disrupting step lyses the cell membrane and inclusion body of the host cell, releasing the insoluble precipitate from the inclusion body and maintaining its insoluble state. In one embodiment, the insoluble precipitate released in the disrupting step is recovered through centrifugation. Therefore, the step of obtaining the precipitated fusion protein by changing environmental conditions (e.g., temperature, ion concentration, pH value and the like) is omitted, and the influence of severe environmental condition changes on the stability and activity of the protein is also avoided.

In one embodiment, resuspending the obtained insoluble precipitate at the second pH value and recovering the supernatant containing the molecule of interest. Therefore, subsequent purification treatment can be directly carried out without high salt concentration, and thus avoiding ion residues, reducing operation times and reducing cost.

In another aspect, the present invention relates to a method for purifying a molecule of interest from a sample, comprising the steps of: (a) providing a sample containing the fusion protein according to any of the preceding embodiments; (b) collecting the fusion protein by means of a purification tag; (c) adjusting pH value such that the molecule of interest is cleaved from the fusion protein; and (d) recovering the molecule of interest. In one embodiment, the step (c) comprises a step of adjusting pH value of a solution containing the fusion protein collected from step (b) such that the molecule of interest is cleaved from the fusion protein.

In one embodiment, the purification tag is an affinity tag, and the collecting the fusion protein according to step (b) is completed by affinity chromatography, and the recovering the molecule of interest according to step (d) is completed by an elution chromatography column. In one embodiment, the purification tag is an aggregating tag, collecting the fusion protein according to step (b) is completed by centrifuging the insoluble precipitate formed by aggregation of the aggregating tag, and the step (d) separates the molecule of interest dissolved in the supernatant from the insoluble precipitate by centrifuging. In a specific embodiment, the aggregating tag is an amphipathic self-assembling short peptide. In one embodiment, the self-assembling short peptide of the present invention is selected from: 18A (DWLKAFYDK-VAEKLKEAF) (SEQ ID NO:45), ELK16 (LELELKLKLELELKLK) (SEQ ID NO:46), $L_6KD$ (LLLLLLKD) (SEQ ID NO:47), EFR8 (FEFRFEFR) (SEQ ID NO:48) and EFK8 (FEFKFEFK) (SEQ ID NO:49). In a specific embodiment, the self-assembling short peptide of the present invention is $L_6KD$ (LLLLLLKD) (SEQ ID NO:47).

In one embodiment, adjusting pH value in step (c) comprises adjusting the pH from the first pH value to the second pH value. In one embodiment, the first pH value is neutral to weakly basic. In a specific embodiment, the first pH value is 7.2-8.5. In a preferred embodiment, the first pH value is 7.4-7.8. In a more preferred embodiment, the first pH value is 7.4-7.6. In the most preferred embodiment, the first pH value is 7.5. In one embodiment, the second pH value refers to a pH value which is weakly acidic. In a preferred embodiment, the second pH value is 5.5-6.8, and preferably 5.5-6.5. In the most preferred embodiment, the second pH value is 6.0.

In another aspect, the present invention also relates to a method for screening a polypeptide for producing or purifying a molecule of interest, comprising the following steps: (a) preparing a fusion protein comprising a variant of the Mtu ΔI-CM intein set forth in SEQ ID NO:1 or a biologically active fragment of the variant, and the molecule of interest attached to the C terminus thereof; and (b) under the condition that the fusion protein has biological activity, screening the polypeptide with reduced C-terminal cleavage efficiency at pH 7.2-8.5 and similar or increased C-terminal cleavage efficiency at pH 5.5-6.8 as compared with the Mtu ΔI-CM intein set forth in SEQ ID NO:1, wherein the N-terminal cleavage activity of the variant or biologically active fragment of the variant is silenced. In one embodiment, the fusion protein in step (a) further comprises a tag protein located at the N terminus. In a preferred embodiment, the tag protein is a fluorescent protein.

In one embodiment, the variant or the biologically active fragment of the variant comprises one or more mutations as compared with the Mtu ΔI-CM intein set forth in SEQ ID NO:1. In a preferred embodiment, the mutations are one or more amino acid substitutions at sites corresponding to the sites within the range of 5 Å around H157 and H167 of the sequence set forth in SEQ ID NO:1.

Unless otherwise defined, scientific and technical terms used in connection with the present invention shall have the meanings commonly understood by those of ordinary skill in the art. Unless otherwise defined, the methods and techniques of the present invention are generally performed according to methods known and conventional in the art. Unless otherwise defined, when the term "a" or "an" is used herein, they mean "at least one" or "one or more". In addition, unless otherwise defined, singular terms and their corresponding plural forms are used interchangeably herein. Except for examples or otherwise stated, all numbers describing amounts of ingredients, reaction conditions and the like used in this specification and claims should be interpreted to be modified by the term "about" in all cases. Therefore, unless indicated to the contrary, the numerical parameters described in the specification and claims are approximations. All publications cited herein are incorporated herein by reference in their entirety.

EXAMPLES

In order to make the embodiments and advantages of the present invention clearer, the executive mode of the present invention will be described in further details below through working examples. It should be understood that the working examples should not be construed as limiting, and those skilled in the art can further adjust the examples based on the principles of the present invention.

Methods used in the following working examples are conventional methods unless otherwise specified. For specific steps, see, for example, "Molecular Cloning: A Laboratory Manual" (Sambrook, J., Russell, David W., Molecular Cloning: A Laboratory Manual, 3rd edition, 2001, NY, Cold Spring Harbor). All the primers were synthesized by Invitrogen.

Example 1: Construction of Expression Vector for CFP-Mtu ΔI-CM-YFP Screening System As shown in FIG. 1, based on the work of Amitai et al. (Amitai et al., Proc. Natl. Acad. Sci., USA, 106: 11005 (2009)), a high throughput screening method based on 96-well plates and fluorescence resonance energy transfer (FRET) was established by the inventors. The N terminus and the C terminus of an Mtu ΔI-CM intein are connected with cyan fluorescent protein (CFP) and yellow fluorescent protein (YFP) respectively. FRET will occur when the distance between CFP and YFP is less than 100 Å. It was found that the distance between A1 at the N terminus of Mtu ΔI-CM and N168 at the C terminus of Mtu ΔI-CM is 9 Å, and thus FRET should occur in this construction.

In the present example, a CFP-Mtu ΔI-CM-YFP (C-I-Y) positive control system and a CFP-Mtu ΔI-CM (N168A)- le;.4qYFP (C-Ia-Y) negative control system are constructed. In the positive control system, a Mtu ΔI-CM intein with C-terminal cleavage activity was used, while in the negative control system, a Mtu ΔI-CM intein (N168A) with silenced C-terminal cleavage activity was used. Premature cleavage of the positive control intein in vivo would lead to a decrease in FRET intensity, while in the negative control intein, no cleavage occurred in vivo, so FRET intensity was stronger, as shown in FIG. 1. The specific construction method is described as follows.

The amino acid sequence encoding Mtu ΔI-CM intein was obtained from the NCBI database, and mutations (C1A, V67L and D150G) made by the Wood group were introduced into its amino acid sequence (168 aa) to obtain the Mtu ΔI-CM intein amino acid sequence. The gene of the Mtu ΔI-CM intein was synthesized by Nanjing GenScript Biotech Corp. after codon optimization according to codon bias of *Escherichia coli*, and then was inserted into a pUC18 plasmid.

CFP-YFP genes were synthesized by Nanjing GenScript Biotech Corp. after codon optimization according to codon bias of *Escherichia coli*, and were inserted between NdeI and XhoI sites of a pET30(a) plasmid, which results in pET30(a)-CFP-YFP. There is a gene sequence of GSGGS-EcoRI-HindIII-GSGGS between CFP and YFP genes, in which the Mtu ΔI-CM intein is inserted between the EcoRI and HindIII restriction sites.

Primers shown in Table 3 were designed and synthesized using Oligo 7 software. Using pUC18-Mtu ΔI-CM plasmid constructed by Nanjing GenScript Biotech Corp. as the template, N-Mtu in Table 3 as the forward primer, Mtu-down-positive-FRET or Mtu-down-negative-FRET as the reverse primer, PCR amplification was carried out according to conventional methods to obtain Mtu ΔI-CM and Mtu ΔI-CM (N168A) polynucleotide fragments with EcoRI and HindIII restriction sites located upstream and downstream respectively. The PCR reaction system and reaction program are shown in Table 4. After the reaction was completed, PCR amplification products were analyzed using 1% agarose gel electrophoresis, and the results showed that PCR amplified the correct bands as expected.

TABLE 3

Sequences of Primers Used in the Present Example

| SEQ ID NO: | Primer Name | Sequence [a] | Description |
|---|---|---|---|
| 19 | N-Mtu | 5'-CCG<u>GAATTC</u>GCGCTGGCTGAAG GCACCGCATTT-3' (EcoRI) | positive control primer to amplify Mtu ΔI-CM gene |
| 20 | Mtu-down-positive-FRET | 5'-CCC<u>AAGCTT</u>GTTATGAACCACAA CGCCTTCCGCAACCAG-3' (HindIII) | |
| 21 | Mtu-down-negative-FRET | 5'-CCC<u>AAGCTT</u>GGCATGAACCACA ACGCCTTCCGCAACCAG-3' (HindIII) | negative control primer, using No. 19 as the forward primer to amplify Mtu ΔI-CM (N168A) gene |

[a] The underlined nucleotides in the sequence represent the corresponding restriction enzyme recognition sites stated in brackets. If no special explanation, the same below.

TABLE 4

Reaction System and Program for Amplifying Mtu ΔI-CM Intein

| Reagents | Volume (μL) |
|---|---|
| 5 × Q5 buffer | 20 |
| dNTPs (2.5 mM) | 8 |
| Template DNA(1 ng/μL) | 2 |
| forward primer (20 μM) | 2.5 |
| reverse primer (20 μM) | 2.5 |
| Q5 high fidelity DNA polymerase | 1 |
| sterilized distilled water | Add up to 100 |

| Reaction program |
|---|
| 1. 98° C. 30 s |
| 2. 98° C. 10 s |
| 3[a]. 68° C. 30 s |
| 4[a]. 72° C. 44 s |
| 5. return to 2, repeat 34 cycles |
| 6. 72° C. 5 min |

[a]The annealing temperature is Tm of forward and reverse primers plus 5° C., and the extension time is 30 s/Kb.

The two gene fragments were subjected to double enzyme digestion by EcoRI and HindIII enzymes, and ligated with the vector pET30(a)-CFP-YFP digested by the same endonucleases, and then, the ligation product was transformed into *Escherichia coli* BL21 (DE3) (Novagen) competent cells, and the transformed cells were spread on LB plates containing 50 μg/mL Kanamycin for positive clones screening. Then the plasmids of the positive colonies were extracted and sequenced. The sequencing results showed that the sequences of the constructs pET30a(+)-C-I-Y and pET30a(+)-C-Ia-Y were correct.

Example 2: Expression of Screening System in 96-Well Plates and FRET Determination Method In Vitro and In Vivo Recombinant bacteria *E. coli* BL21(DE3)/pET30a(+)-C-I-Y and *E. coli* BL21(DE3)/pET30a(+)-C-Ia-Y were inoculated on LB plates containing Kanamycin (50 μg/mL) and cultivated overnight at 37° C. The C-I-Y mutant strains and the positive and negative control strains were inoculated into a 96-well plate containing 200 μL of LB medium (50 μg/mL Kanamycin), and the plate was placed in a shaker (250 rpm) and cultivated overnight at 37° C. 10 μL of each culture was transferred to a new 96 deep-well plate containing 500 μL of LB (50 μg/mL Kanamycin). When the OD600 reached 0.4-0.6 absorbance units (AU), a final concentration of 0.2 mM IPTG (isopropyl β-D-I-thiogalactopyranoside) was added to initiate protein expression. The cultures of C-I-Y mutant strains and control strains were then continued for expression for 26 h at 30° C. (250 rpm).

After the expression is completed, the method for determination FRET in vivo in a 96-well plate is as follows: the culture was diluted with an equal volume of LB medium and transferred to a black flat-bottomed 96-well assay plate. The samples were screened for cleavage activity by excitation of the liquid cultures at 390 nm and monitoring the fluorescence emission in the range 460-555 nm with an Infinite M200 microplate reader (TECAN, Zürich, Switzerland). A method for determining FRET in vitro via a 96-well plate is as follows: after expressed by the above method, cells were first harvested by centrifugation at 4° C. 3,000×g for 10 min. The pellets were subjected to three freeze-thawing cycles, and then the proteins were extracted by treating the pellets with 30 μL of B-PER-II for every 500 μL of liquid culture. The samples were then incubated at room temperature for 15 min, during which the cells were disrupted for protein extraction. Then the samples were centrifuged at 15,000×g for 10 min at 4° C. to separate the supernatant and the precipitate. For each analysis, 10 µL of supernatant containing the C-I-Y fusion protein was added to 190 µL of intein cleavage buffer (buffer B4, 50 mM Na$_2$HPO$_4$—NaH$_2$PO$_4$, pH 6.0) in each well of the black flat-bottomed 96-well assay plates, to initiate the cleavage of interns of C-I-Y fusion proteins. The intein cleavage reaction was performed by incubating the samples at 25° C. for 3 h, and continued at 4° C. overnight, with shaking (250 rpm). The in vitro FRET emission was determined by an Infinite M200 microplate reader (TECAN, Zürich, Switzerland) using the same method as described for the in vivo FRET assay.

Figure 2:
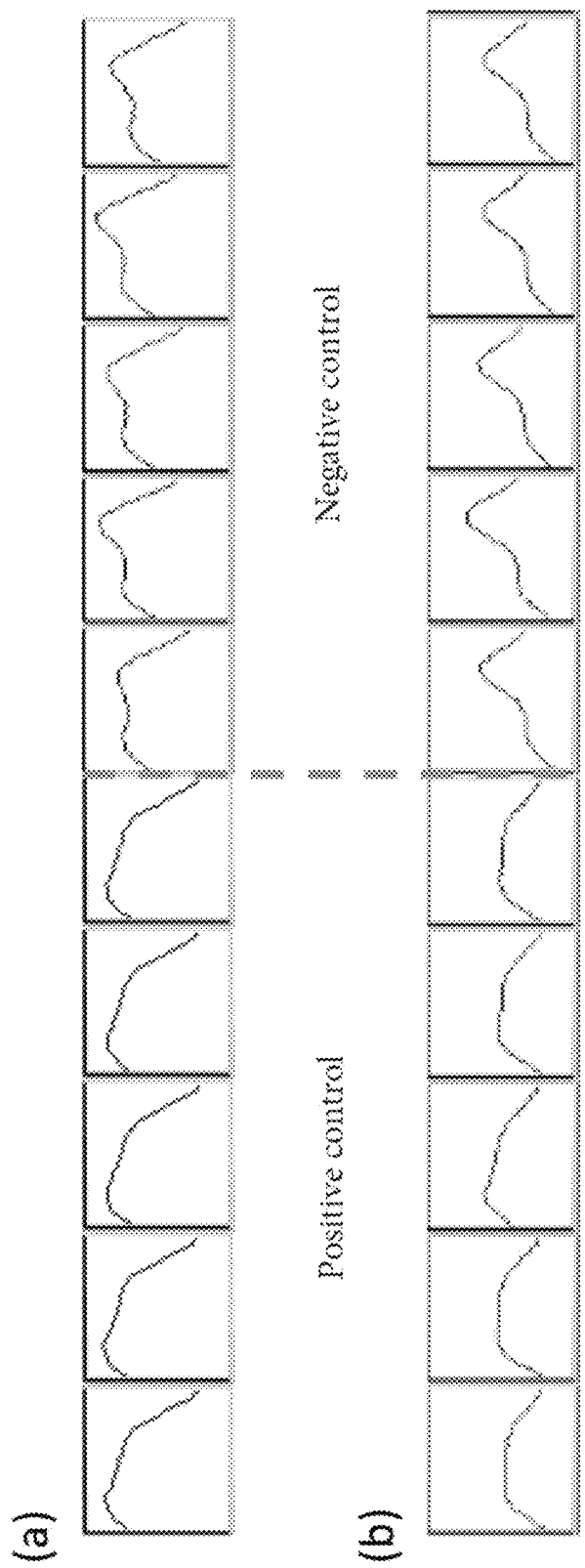
FIG. 2 shows FRET spectrograms of positive and negative controls in a 96-well plate in vivo and in vitro, wherein (a) is a FRET spectrogram of the positive and negative controls in vivo, and (b) is a FRET spectrogram of the positive and negative controls in vitro; and abscissae are emission wavelength (nm) and ordinates are fluorescence intensity (RFU).

In vivo and in vitro FRET spectra of the positive control and the negative control are shown in FIG. 2 (each selected 5 colonies respectively), and there are obvious differences between positive and negative controls both in vivo and in vitro.

Example 3: Semi-Rational Design of Mtu ΔI-CM Intein

The invention utilizes a semi-rational design method to carry out site selection on the Mtu ΔI-CM intein.

The inventors speculate that four conservative amino acids play a key role in C-terminus cleavage of Mtu ΔI-CM, namely, D422 in the F-block of the original Mtu RecA maxi-intein (mutated into Gly by Wood et al., which cuts off the link between C-terminal cleavage and N-terminal cleavage and facilitates C-terminal cleavage, corresponding to G150 in SEQ ID NO:1), H429 in the F-block (corresponding to H157 in SEQ ID NO:1), H439 in the G-block (corresponding to H167 in SEQ ID NO:1) and N440 (corresponding to N168 in SEQ ID NO:1).

According to the possible cleavage mechanism, the inventors speculate that the pKa values of H157 and H167 residues may affect the pH-inducible cleavage of the Mtu ΔI-CM intein at the C-terminus. Since hydrogen bonds, charge interactions, solvation effects, etc. can affect the pKa values of amino acids, especially charge effects and hydrogen bonds, the inventors therefore envisage to change the pKa values of H157 and H167 residues by changing the amino acids around H157 and H167, and thereby obtaining a Mtu ΔI-CM mutant strain with reduced cleavage efficiency in E. coli cells (pH 7.4-7.8), but still capable of efficient cleavage at pH 6.0 in vitro. In this example, amino acids within the range of 5 Å around H157 and H167 were selected for site-specific saturated mutations, mainly aiming at amino acids which may form hydrogen bonds or have a charge effect. It was found that there are 9 amino acids within the range of 5 Å around H157, namely E152, V153, E154, E155, L156, T158, L159, V166 and H167; and there are 10 amino acids within the range of 5 Å around H167, namely L2, H73, K74, V75, W81, H157, T158, L159, V165 and V166. The inventors first selected the polar amino acid E152, E154, E155, T158, H73 and K74 for mutation.

Example 4: Construction of Site-Directed Saturated Mutagenesis Library

By using the Mtu ΔI-CM intein as a template and with an NNK degenerate codon (N represents a mixture of 4 bases: A, G, C and T, and K represents a mixture of 2 bases: G and T), 20 amino acids were introduced into the 6 sites described in Example 3 to establish a site-directed saturation mutagenesis (SDSM) library at each site. The primers used are shown in Table 5. Taking the SDSM library at T158 and H73 as an example, the process of establishing the library is illustrated as follows.

TABLE 5

Sequences of Primers Used in Construction of Site-directed Saturated Mutation Library

| SEQ ID NO: | Primer Name | Sequence $^a$ | Description |
|---|---|---|---|
| 22 | Mtu-down-E152 | 5'-CCC<u>AAGCTT</u>GTTATGAACCACAACGCCTTCCGCAACCAGGGTATGCAGTTCTTCCACMNNCAGACCAAACGTGCG-3' (HindIII) | reverse primer for the construction of mutation library at E152 |
| 23 | Mtu-down-E154 | 5'-CCC<u>AAGCTT</u>GTTATGAACCACAACGCCTTCCGCAACCAGGGTATGCAGTTCMNNCACTTCCAGACC-3' (HindIII) | reverse primer for the construction of mutation library at E154 |
| 24 | Mtu-down-E155 | 5'-CCC<u>AAGCTT</u>GTTATGAACCACAACGCCTTCCGCAACCAGGGTATGCAGMNNTTCCACTTCCAGACC-3' (HindIII) | reverse primer for the construction of mutation library at E155 |
| 25 | Mtu-down-T158 | 5'-CCC<u>AAGCTT</u>GTTATGAACCACAACGCCTTCCGCAACCAGMNNATGCAGTTCTTCCA-3' (HindIII) | reverse primer for the construction of mutation library at T158 |
| 26 | Mtu-up-H73 | 5'-GGCAACCCCGGATNNKAAAGTGCTGACGGAATATG-3' | overlapping PCR primers for the construction |
| 27 | Mtu-down-H73 | 5'-TCCGTCAGCACTTTMNNATCCGGGGTTGCCCACAGAATTGCAC-3' | construction of mutation library at H73 |
| 28 | Mtu-up-K74 | 5'-GGCAACCCCGGATCATNNKGTGCTGACGGAATATGGCTGGCGTG-3' | overlapping PCR primers for the construction |
| 29 | Mtu-down-K74 | 5'-TATTCCGTCAGCACMNNATGATCCGGGGTTGCCCACAGAATTG-3' | construction of mutation library at K74 |
| 30 | C-Mtu | 5'-CCC<u>AAGCTT</u>GTTATGAACCACAACGCCTTCCGCAACCAG-3' (HindIII) | reverse primer for the construction of mutation libraries of H73 and K74 |

$^a$ Nucleotides bolded in the sequence are degenerate codons NNK and MNN. NNK was used in forward primers for site-directed saturated mutations; and MNN was used in reverse primers for site-directed saturated mutations, wherein M represents a mixture of two bases: C and A.

For the construction of T158 library, using pUC18-Mtu ΔI-CM plasmid as the template and N-Mtu and Mtu-down-T158 in Table 5 as forward and reverse primers, a Mtu ΔI-CM gene fragment with saturated mutations at T158 was obtained through amplification. The PCR reaction system and reaction program are shown in Table 6. After the reaction was completed, PCR amplification products were analyzed using 1% agarose gel electrophoresis, and the results showed that correct bands were amplified as expected. The expected amplified fragments harbored the EcoRI and HindIII recognition sites at the upstream and downstream, respectively. After purifying the fragments by DNA gel recovery, the gene fragment was double digested with EcoRI and HindIII enzymes, then was ligated to the vector pET30(a)-CFP-YFP that was double digested by the same endonuclease and dephosphorylated, and meanwhile, a ligation reaction without adding the digested gene fragment was used as a negative control (for vector self-ligation). The target and control ligation products were transformed into *E. coli* BL21(DE3) to obtain a SDSM library of Mtu ΔI-CM at T158. On the LB plate, the number of colonies of the SDSM library at T158 was about 700, while the number of colonies of the negative control was only 7, which indicated that the SDSM library was constructed at a high efficiency of cloning and can be used for further screening. The construction of SDSM libraries at E152, E154 and E155 was the same as that for T158.

TABLE 6

Reaction System and Program for Amplifying Mtu ΔI-CM Mutant Strain at T158

| Reagents | volume (µL) |
|---|---|
| 5 × Q5 buffer | 20 |
| dNTPs (2.5 mM) | 8 |
| Template DNA (1 ng/µL) | 2 |
| forward primer (20 µM) | 2.5 |
| reverse primer (20 µM) | 2.5 |
| Q5 high fidelity DNA polymerase | 1 |
| sterilized distilled water | Add up to 100 |

| Reaction Program |
|---|
| 1. 98° C. 30 s |
| 2. 98° C. 10 s |
| 3$^a$. 68° C. 30 s |
| 4$^a$. 72° C. 44 s |
| 5. return to 2, repeat 34 cycles |
| 6. 72° C. 5 min |

$^a$The annealing temperature is Tm of forward and reverse primers plus 5° C., and the extension time is 30 s/Kb.

For the construction of H73 library, also chose pUC18-Mtu ΔI-CM plasmid as the template, according to the PCR system and program shown in Table 6, chose N-Mtu and Mtu-down-H73 in Table 5 as forward and reverse primers to amplify the upstream fragment carrying H73 mutations, and chose Mtu-up-H73 and C-Mtu as forward and reverse primers respectively to amplify the downstream fragment harboring H73 mutations. Used equimolar mixed two fragments solution as the template, overlap-extended the full-length gene. After 19 cycles of reaction without primer addition, primers N-Mtu and C-Mtu were added to continue the reaction for 34 cycles. The specific reaction system and program are shown in Table 7. The full-length Mtu ΔI-CM gene with saturated mutation at H73 was obtained. The remaining steps are the same as those for T158. The construction of SDSM library at K74 is the same as that for H73. Six SDSM libraries were established above for further screening.

TABLE 7

Reaction System and Program of Overlapping PCR for Amplifying Mtu ΔI-CM

Mutant Strain at H73

| Reagents | Volume (µL) |
|---|---|
| 5 × Q5 buffer | 20 |
| dNTPs (2.5 mM) | 8 |
| upstream fragment | 40 ng |
| downstream fragment | 60 ng |
| forward primer (20 µM) $^a$ | — |
| reverse primer (20 µM) $^a$ | — |
| Q5 high fidelity DNA polymerase | 1 |
| sterilized distilled water | Add up to 100 |

| Reaction program step 1 | Reaction program step 2 |
|---|---|
| 1. 98° C. 30 s | 1. 98° C. 30 s |
| 2. 98° C. 10 s | 2. 98° C. 10 s |
| 3. 68° C. 30 s | 3. 68° C. 30 s |
| 4. 72° C. 20 s | 4. 72° C. 20 s |
| 5. return to 2, repeat 19 cycles | 5. return to 2, repeat 34 cycles |
| 6. 72° C. 5 min | 6. 72° C. 5 min |

$^a$ After step 1 is completed, add the forward and reverse primers to the reaction system, and then perform step 2.

Example 5: Screening of Site-Directed Saturated Mutagenesis Library

Using the screening method established in Example 2, six saturated libraries were screened by an Infinite M200 microplate reader (TECAN, Zürich, Switzerland), and 180 colonies (two 96-well plates) were selected from each library with a mutation coverage rate of 99%. The screening procedure is as follows: firstly, preliminary screening was carried out on a 96-well plate. Single colony in the SDSM library were first streaked on LB plates (containing 50 µg/mL Kanamycin) for backup, and then inoculated into the 96-well plate containing 200 µL LB medium (containing 50 µg/mL Kanamycin), and at the same time two mocks (only LB medium), two positive controls and two negative controls were inoculated, and cultivated overnight at 37° C. with shaking (250 rpm). 10 µL of each culture from each well was transferred to a new 96 deep-well plate containing 500 µL of LB per well. When the OD600 reached 0.4-0.6 AU, a final concentration of 0.2 mM IPTG was added to the cultures. The cultures were then continued for further cultivation for 26 h at 30° C. with shaking (250 rpm) to induce C-I-Y mutant expression. After expression, FRET was determined in vivo and in vitro respectively according to the method described in Example 2. The results of FRET determination in vivo and in vitro were compared and analyzed. Mutant strains with obvious FRET in vivo (comparable to the negative control) but obsolete FRET in vitro (comparable to the positive control) were selected. Re-screened 96-well plate in triplicate, and the screening procedure was the same as the initial screening procedure. The mutant strains obtained by re-screening the 96-well plate were sequenced to identify the genotype alteration. After excluded variants with the same genotype, the resulting variants were then further confirmed in test tube in triplicate.

Figure 3:
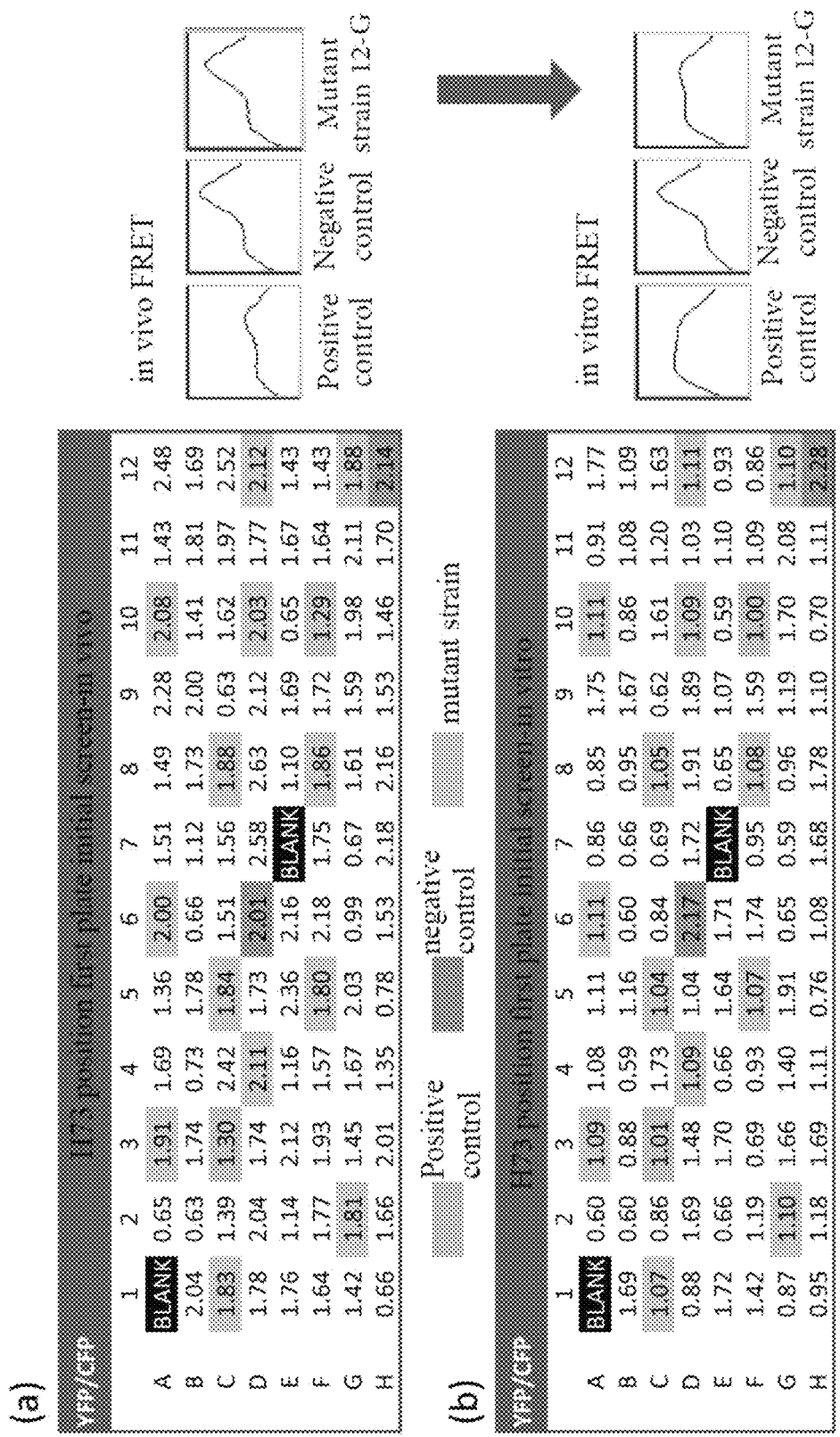
FIG. 3 shows the preliminary screening results of a first 96-well plate at the H73 site, wherein (a) is the in vivo preliminary screening result of the first 96-well plate at the H73 site, with the right pane showing the FRET spectrograms of the positive and negative controls and a mutant strain 12-G in vivo; (b) is the in vitro preliminary screening result of the first 96-well plate at the H73 site, with the right pane showing the FRET spectrograms of the positive and negative controls and the mutant strain 12-G in vitro; and C3 and F10 show the positive control, D6 and H12 show the negative control, and the remaining gray markers show the other screened mutant strains.

According to the screening procedure in Example 2, each library was first subjected to 96-well plate preliminary screening. As shown in FIG. 3, the preliminary screening result of the first 96-well plate at site H73 was characterized by the value of YFP/CFP, wherein C3 and F10 show the positive controls, D6 and H12 show the negative controls, and the remaining gray markers show the mutant strains obtained by preliminary screening. It was found that there were indeed some mutant strains with reduced cleavage efficiency in vivo (YFP/CFP value close to the negative control), but maintain high cleavage efficiency in vitro (YFP/CFP value close to the positive control), such as mutant strain 12-G. After re-screened the mutant strains obtained by preliminary screening in triplicate, sequenced and excluded the variants with the same genotype, and verified the resulting variants in test tube in triplicate, 5 mutant strains were finally obtained with better performance, namely H73Y, H73V, K74N, E154S and T158S. These five mutations occur at four different sites, of which two are at the site 73.

Figure 4:
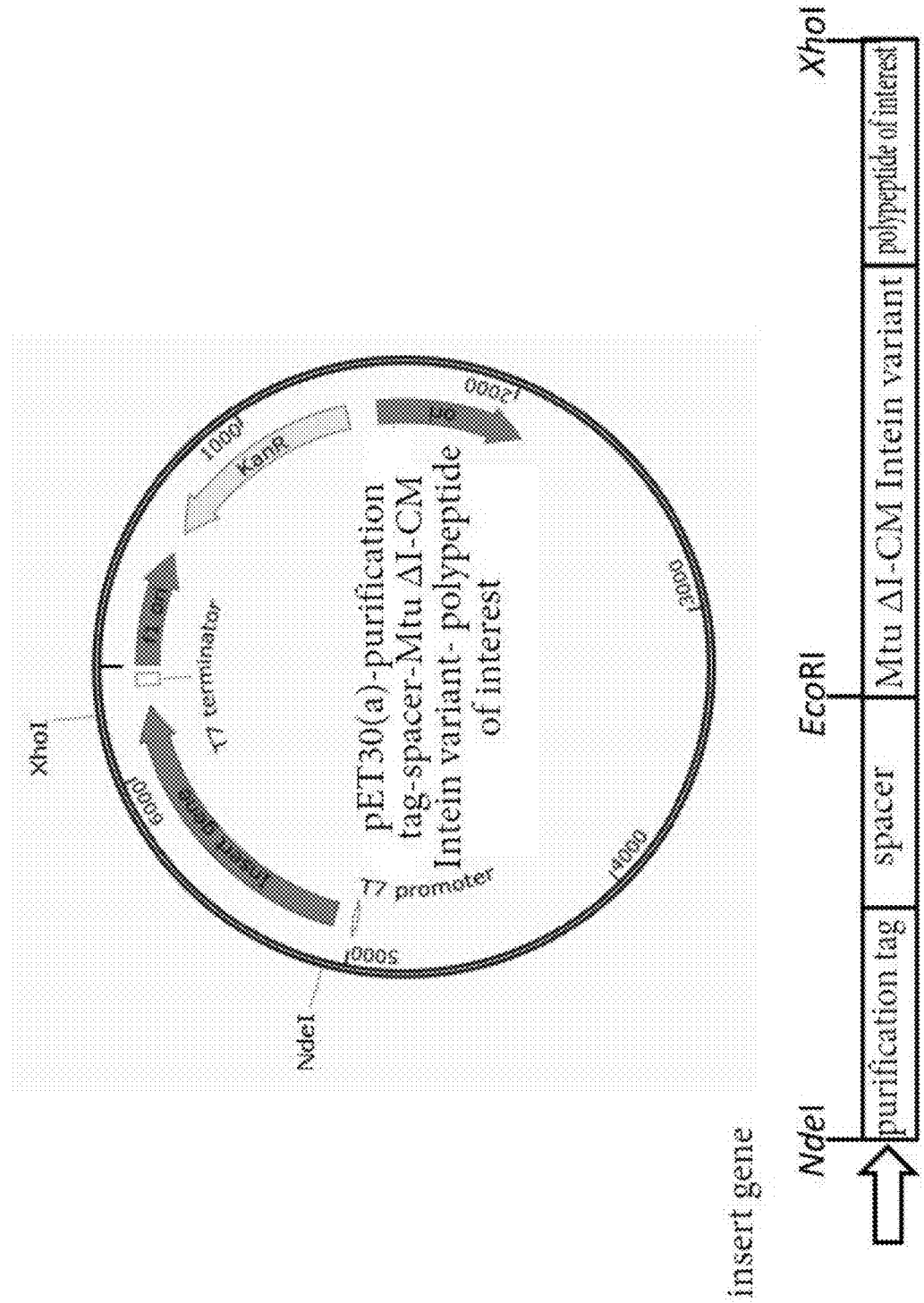
FIG. 4 shows a map of a fusion protein expression vector of the present invention.
Figure 5:
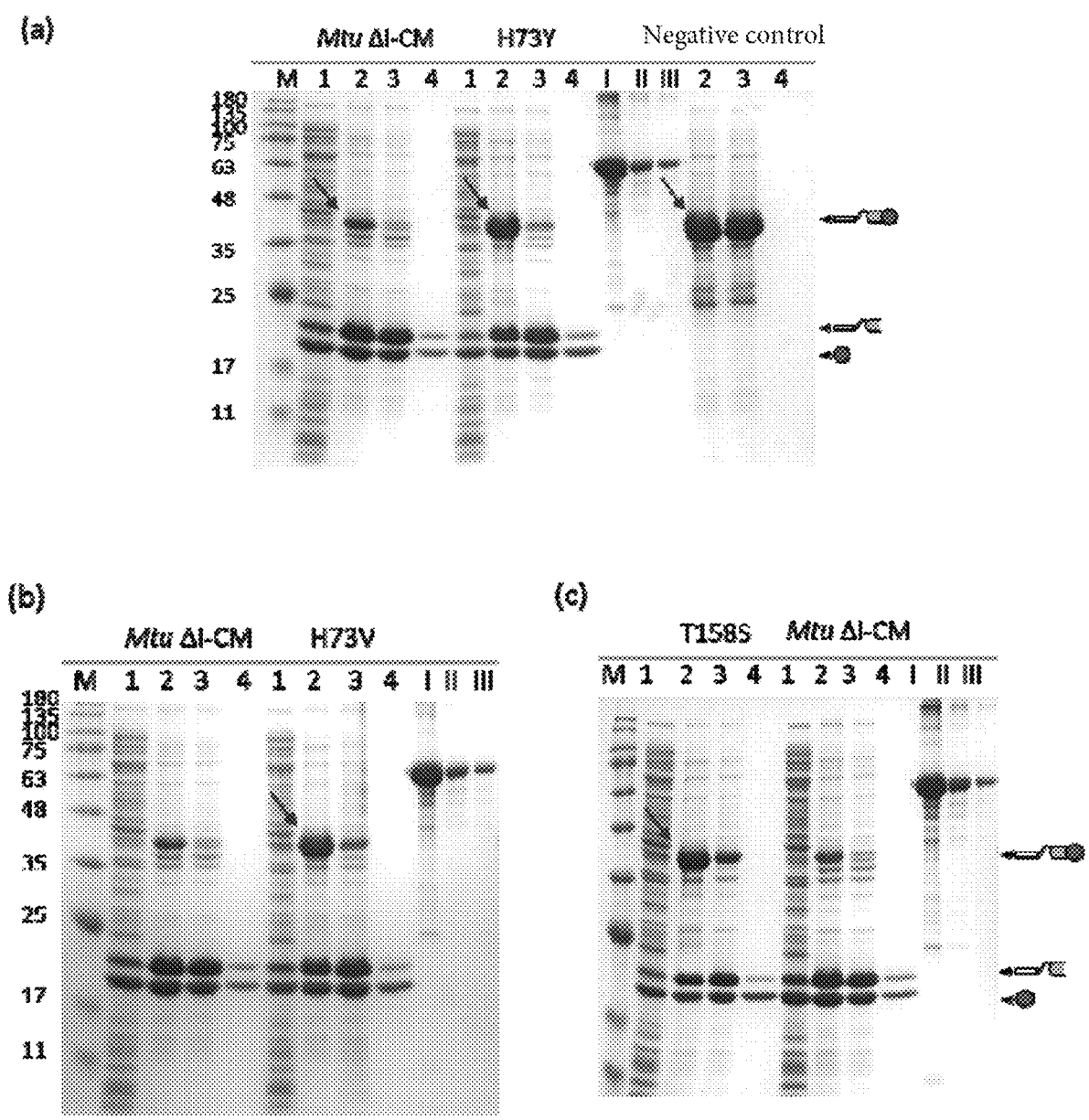
FIG. 5 shows the detection results of single mutant strains in the L6KD-I-LipA system, wherein (a) to (e) are the verification results of variants H73Y, H73V, T158S, K74N and E154S in the L6KD-I-LipA system, respectively; lane 1 is the supernatant of cell lysate; lane 2 is the precipitate of cell lysate; lane 3 is the precipitate after cleavage; lane 4 is the supernatant after cleavage; and lanes I, II and III are BSA standards (concentrations of BSA are 1000, 250 and 125 µg/ml, respectively).
Figure 5:
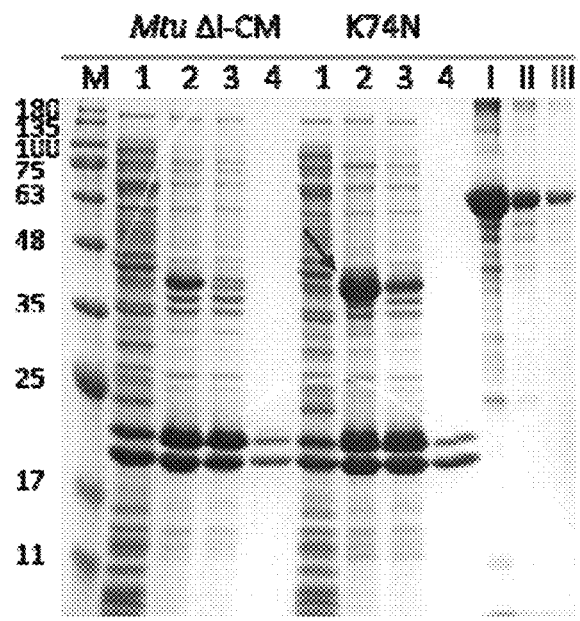
Figure 5:
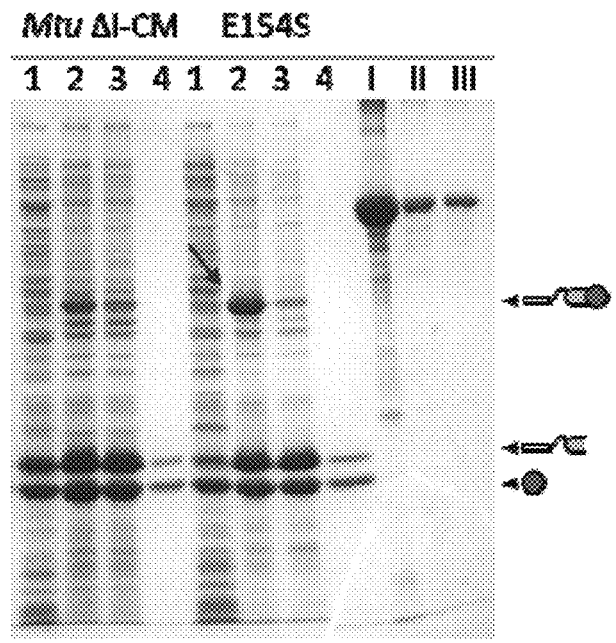

Example 6: Verification of Single Site Mutant Strain in $L_6KD$-I-LipA Protein Purification System The Mtu ΔI-CM mutant strains screened in Example 5 were first constructed into the $L_6KD$-I-LipA system (LipA is of 191aa, the amino acid sequence of which is set forth in SEQ ID NO:50, and the nucleotide sequence of which is set forth in SEQ ID NO:52) for verification. The construction map is shown in FIG. 4. The primers used for construction are shown in Table 8. The plasmids pET30a-C-I(mutant)-Y in the selected mutant strains in Example 5 were extracted, and then were used as the template to amplify the upstream fragment I(mutant) of I(mutant)-LipA by using N-Mtu and Mtu-LipA-down in Table 8 as forward and reverse primers according to the PCR reaction system and program shown in Table 4. Meanwhile, pET30a-$L_6$KD-1-LipA plasmids were used as the template to amplify the downstream fragment LipA of I(mutant)-LipA by using Mtu-LipA-up and C-LipA as forward and reverse primers. According to the overlapping PCR reaction system and program shown in Table 9, the complete I(mutant)-LipA gene were amplified. The fragments were subjected to double enzyme digestion with EcoRI and XhoI enzymes, and ligated to the vector pET30a-$L_6$KD-I-LipA digested by the same endonucleases, the ligation product was transformed into *Escherichia coli*. Then the clones were identified by colony PCR and sequencing. In addition, the recombinant plasmid pET30(a)-$L_6$KD-I (N168A)-LipA was constructed by the same method in this study as a negative control for subsequent characterization.

TABLE 8

Sequences of Primers for Amplification of I (mutant)-LipA

| SEQ ID NO: | Primer Name | Sequence | Description |
|---|---|---|---|
| 31 | Mtu-LipA-up | 5'-TTGTGGTTCATAACCACCATCACCATCACCACCCCAC-3' | overlapping PCR primers for the construction of I (mutant)-LipA |
| 32 | Mtu-LipA-down | 5'-GATGGTGATGGTGGTTATGAACCACAACGCCTTCCGCAA-3' | overlapping PCR primers of I (mutant)-LipA |
| 33 | Mtu-LipA-negative-up | 5'-TTGTGGTTCATGCCCACCATCACCATCACCACCCCAC-3' | overlapping PCR primers for the construction of negative control I |
| 34 | Mtu-LipA-nega- | 5'-GTGATGGTGATGGTGGGCATGAACCACAACGCCTTCC |  |

TABLE 8-continued

Sequences of Primers for Amplification of I (mutant)-LipA

| SEQ ID NO: | Primer Name | Sequence | Description |
|---|---|---|---|
|  | tive-down | GCAA-3' | (N168A)-LipA |
| 35 | C-LipA | 5'-AGTCTA<u>CTCGAGT</u>CAATTCGTATTCTGGCCCCCGCCGTTC-3' (XhoI) | reverse primers for the construction of $L_6$KD-I (mutant)-LipA and negative control system |

TABLE 9

Overlapping PCR Reaction System and Program for Amplifying I(mutant)-LipA

| Reagents | volume (μL) |
|---|---|
| 5 × Q5 buffer | 20 |
| dNTPs (2.5 mM) | 8 |
| upstream fragment | 40 ng |
| downstream fragment | 60 ng |
| forward primer (20 μM) [a] | — |
| reverse primer (20 μM) [a] | — |
| Q5 high fidelity DNA polymerase | 1 |
| sterilized distilled water | Add up to 100 |

| Reaction program step 1 | Reaction program step 2 |
|---|---|
| 1. 98° C. 30 s | 1. 98° C. 30 s |
| 2. 98° C. 10 s | 2. 98° C. 10 s |
| 3. 68° C. 30 s | 3. 68° C. 30 s |
| 4. 72° C. 40 s | 4. 72° C. 40 s |
| 5. return to 2, repeat 19 cycles | 5. return to 2, repeat 34 cycles |
| 6. 72° C. 5 min | 6. 72° C. 5 min |

[a] After step 1 is completed, add the forward and reverse primers to the reaction system, and then perform step 2.

*Escherichia coli* strains with pET30(a)-$L_6$KD-I(mutant)-LipA and control strains were inoculated into LB medium containing 50 μg/mL Kanamycin, and cultivated overnight at 37° C. with shaking (250 rpm). The culture was transferred to LB medium containing 50 μg/mL Kanamycin at a ratio of 1:50, and the expression of recombinant proteins in *E. coli* was induced by 0.2 mM IPTG when the $OD_{600}$ reached 0.4-0.6 (log phase), and IPTG with a final concentration of 0.2 mM was added to induce *Escherichia coli* to express the recombinant protein at 18° C. for 24 h. After expression, measured OD 600 of the bacterial solution under the final concentration, conducted centrifugation at 4° C. 6,000×g for 10 min, and harvested cell pellets and stored in −80° C. refrigerator.

The harvested cell pellets were resuspended in buffer B1 (20 mM Tris-HCl, 500 mM NaCl, 1 mM EDTA, pH 8.5). The cell pellets were placed in an ice-water mixture bath, and followed by sonication to disrupt the cells. For 1 mL 20 $OD_{600}$/mL sample, the disrupting conditions are: I) 2 ultrasonic probe, ultrasonic time 2 s, interval time 2 s, 99 times of cycling, power 100 W (2 s×2 s×99 times). The supernatant fractions were isolated from the pellets by centrifugation at 15,000×g for 20 min at 4° C. The pellets were washed twice with equal volume of buffer B1 to remove soluble impurities in the pellets as much as possible. A certain amount of cell lysate supernatant and pellets sample after wash and resuspension were reserved for subsequent analysis and detection. The pellets obtained above were resuspended with intein cleavage inducing Buffer B2 (50 mM $Na_2HPO_4$—$NaH_2PO_4$ buffer, 500 mM NaCl, pH 6.0) in equal volume, and cleaved at 25° C. for 3 h, and then continued at 4° C. overnight. After cleavage, conducted centrifugation at 4° C. 15,000×g for 20 min to separate the supernatant and pellets, and resuspended the pellets with equal volume of Buffer B1, and then the resuspended pellets together with the supernatant were used for subsequent detection.

Figure 8:
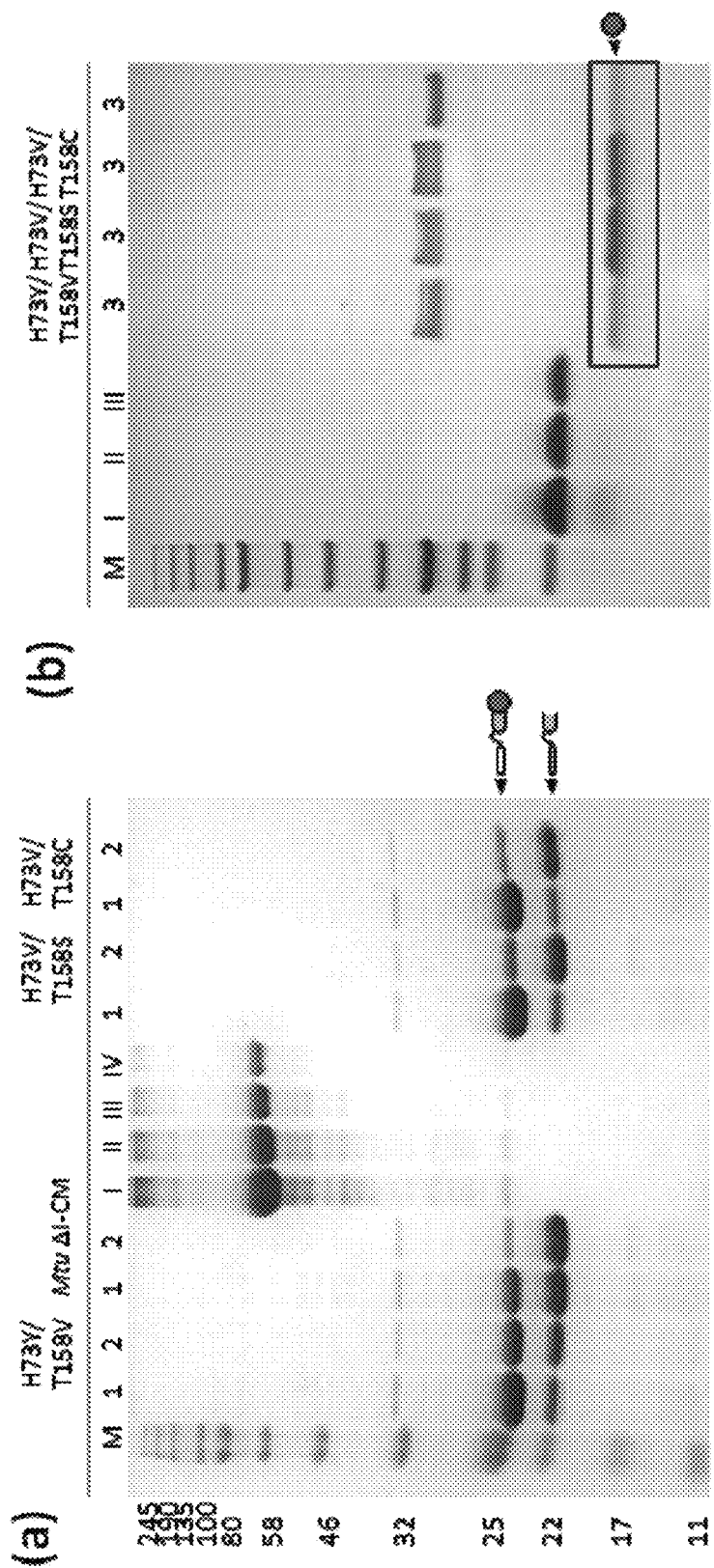
FIG. 8 shows the detection results of double mutant strains in the L6KD-I-GLP1 system, wherein (a) is the results of variants H73Y/T158V, H73V/T158S and H73V/T158C in the L6KD-I-GLP1 system, and (b) is the detection result of the supernatant after cleavage; wherein lane 1 is the precipitate of cell lysate; lane 2 is the precipitate after cleavage; lane 3 is the supernatant after cleavage; and lanes I, II, III and IV are BSA and aprotinin standards (at 1000, 500, 250 and 125 µg/ml for BSA; 250, 125 and 67.5 µg/ml at aprotinin, respectively).

FIG. 8 shows SDS-PAGE detection results of H73Y, H73V, T158S, K74N and E154S mutant strains in the $L_6$KD-I-LipA system respectively. The quantitative results are shown in Table 10.

TABLE 10

Quantification of Variants with Single Mutation in $L_6$KD-I-LipA System

| Variants | Percentage of in vivo cleavage [a] | Aggregate Yield [b] (μg/mg wet cell pellet) | in vitro Cleavage Efficiency [c] | Target Yield [b] (μg/mg wet cell wet pellet) | Advantage [d] |
|---|---|---|---|---|---|
| H73Y | 32% | 43.3 | 92% | 7.9 | 65% |
| H73V | 39% | 32.6 | 81% | 7.2 | 50% |
| T158S | 30% | 40.7 | 75% | 7.7 | 60% |
| K74N | 51% | 37.1 | 80% | 7.6 | 58% |
| E154S | 65% | 22.7 | 86% | 6.0 | 25% |
| Mtu ΔI-CM | 87% | 9.7 | 85% | 4.8 | template |

[a] Percentage of in vivo cleavage, i.e., premature cleavage efficiency of intein, was defined as the mass ratio of the cleaved fusion protein aggregates in vivo over the theoretical value of the fusion protein aggregates.
[b] Calculation was based on "when the concentration of bacterial solution at $OD_{600}$ is 2, the wet cell weight is 2.66 ± 0.99 mg/ml in LB medium".
[c] Cleavage efficiency was defined as the mass ratio of the cleaved fusion protein aggregates in vitro over the fusion protein aggregates actually obtained.
[d] Advantage was defined as (the yield of protein of interest from mutant strain − the yield of protein of interest from Mtu ΔI-CM)/the yield of protein of interest from Mtu ΔI-CM × 100%.

When the 5 mutant strains were applied to the $L_6$KD-I-LipA system, the in vivo premature cleavage efficiency was indeed reduced, and meanwhile the in vitro cleavage efficiency was still maintained, which resulted in the increasing of the yield of LipA protein. Compared with the template Mtu ΔI-CM system, the in vivo cleavage ratio of the fusion protein was decreased from 87% to 30%-65%, and the final LipA yield was increased by 25%-65%, to 6.0-7.9 μg/mg cell wet weight, wherein the in vivo cleavage ratio of the fusion protein in the mutant strain containing H73Y was reduced from 87% to 32%, increasing LipA yield by 65%; the in vivo cleavage ratio of the fusion protein in the mutant strain containing H73V was reduced from 87% to 39%, increasing LipA yield by 50%; and the in vivo cleavage ratio of the fusion protein in the mutant strain containing T158S was decreased from 87% to 30%, increasing LipA yield by 60%, but the in vitro cleavage efficiency of the mutant strain was slightly decreased (from 84% to 75%).

Example 7: Verification of Single Site Mutant Strain in $L_6$KD-I-GLP1 Protein Purification System In this example, the selected 5 single site mutant strains were constructed into the $L_6$KD-I-GLP1 system (GLP1 is of 31aa, the amino acid sequence of which is set forth in SEQ ID NO:51, and the nucleotide sequence of which is set forth in SEQ ID NO:53) to verify if they can also be used for polypeptide preparation efficiently. Refer to the construction of the $L_6$KD-I(mutant)-LipA system in Example 6 for construction method, and the primers used are shown in Table 11.

TABLE 11

Sequences of Primers for Amplification of I (mutant)-GLP1

| SEQ ID NO: | Primer Name | Sequence | Description |
|---|---|---|---|
| 36 | Mtu-GLP1-up | 5'-GTTGTGGTTCATAACCATGCAGAAGGCACCTTTACCA-3' | overlapping PCR primers for the construction of I (mutant)-GLP1 |
| 37 | Mtu-GLP1-down | 5'-GTGCCTTCTGCATGGTTATGAACCACAACGCCTTCCGCAACC-3' | |
| 38 | Mtu-GLP1- | 5'-GCGTTGTGGTTCATGCCCATGC | overlapping PCR primers |

TABLE 11-continued

Sequences of Primers for Amplification of I (mutant)-GLP1

| SEQ ID NO: | Primer Name | Sequence | Description |
|---|---|---|---|
| | negative-up | AGAAGGCACCTTTACCA-3' | for the construction |
| 39 | Mtu-GLP1-negative-down | 5'-GTGCCTTCTGCATGGGCATGAACCACAACGCCTTCCGCAACC-3' | of the negative control I (N168A)-GLP1 |
| 40 | C-GLP1 | 5'-ATCTGA<u>CTCGAG</u>TCAACCACGACCTTTAACCAGCC-3' (XhoI) | reverse primers for the construction of $L_6$KD-I (mutant)-GLP1 and the negative control system |

Figure 6:
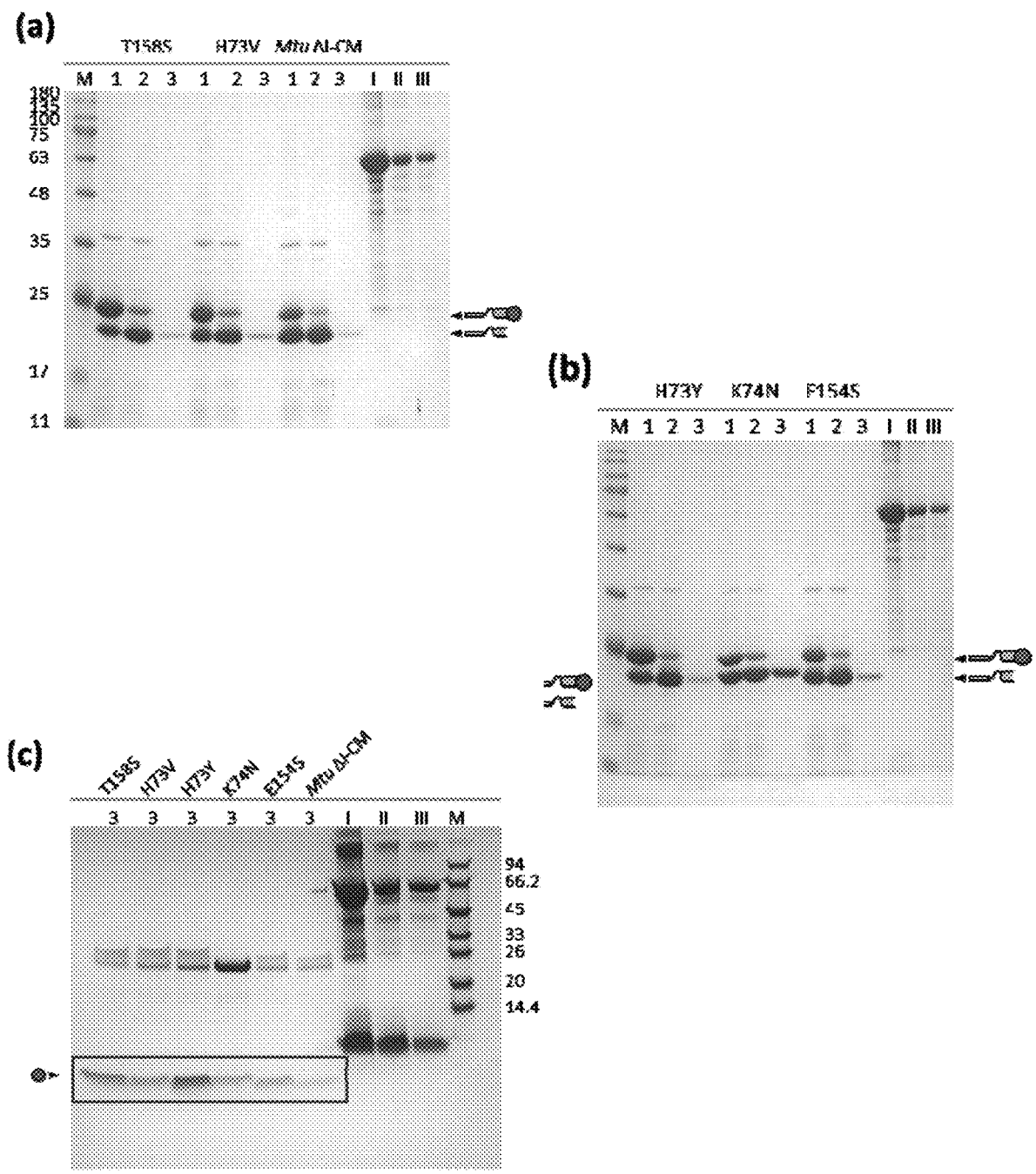
FIG. 6 shows the detection results of single mutant strains in the L6KD-I-GLP1 system, wherein (a) and (b) are the results of variants T158S, H73V, H73Y, K74N and E154S in the L6KD-I-GLP1 system, and (c) is the result of the supernatant after cleavage; lane 1 is the precipitate of cell lysate; lane 2 is the precipitate after cleavage; lane 3 is the supernatant after cleavage; and lanes I, II and III are BSA and aprotinin standards (at 1000, 250 and 125 µg/ml for BSA; and 500, 250 and 125 µg/ml for aprotinin, respectively).

*Escherichia coli* with recombinant plasmid pET30(a)-$L_6$KD-I(mutant)-GLP1 and a control strain were expressed and purified according to the method in Example 6, the obtained samples were analyzed by SDS-PAGE, and the detection results are shown in FIG. 6. Since the supernatant after cleavage (lane 3) contained a GLP-1 band, and the molecular weight of GLP-1 was only 3355.7 Da, which cannot be detected by conventional 12% SDS-PAGE and needed to be detected by 4-12% Bis-Tris SDS-PAGE (FIG. 6 (c)). The quantitative results are shown in Table 12.

Similarly, when the 5 mutant strains were applied to the $L_6$KD-I-GLP1 system, the in vivo premature cleavage efficiency was reduced to different degrees, and the in vitro cleavage efficiency was still maintained in a high level and thus the yield of GLP-1 increased. As shown in Table 12, compared with the original Mtu ΔI-CM system, the application of the mutant strains reduced the in vivo cleavage ratio of the fusion protein in the $L_6$KD-I-GLP1 system from 68% to 31%-54%, and the yield of GLP-1 was increased by 50%-3.3 times, to 1.34-3.92 μg/mg cell wet weight, wherein the in vivo cleavage ratio of the fusion protein in the mutant strain containing T158S was reduced from 68% to 31%, increasing GLP-1 yield by 2.3-fold; the in vivo cleavage ratio of the fusion protein in the mutant strain containing H73V was reduced from 68% to 42%, increasing GLP-1 yield by 1.4-fold, and the in vivo cleavage ratio of the fusion protein in the mutant strain containing H73Y was reduced from 68% to 35%, increasing GLP-1 yield by 3.3-fold. Taken together of the application results of the 5 mutant strains in $L_6$KD-I-LipA system and $L_6$KD-I-GLP1 system, it is found that mutant strains H73Y, H73V and T158S are of better performance.

fragment of the mutation site H73; and meanwhile, used CAST-Mtu-up-73 and Mtu-down-73-158 as forward and reverse primers, and amplified the downstream fragment of the mutation site H73, and the reverse primer Mtu-down-73-158 also introduced mutation into T158. Took an equimolar mixed two fragments as the template, and conducted overlap PCR to amplify a full-length gene. After 19 cycles of reaction without primer addition, primers Mtu-up-73-158 and Mtu-down-73-158 were added to continue the reaction for 34 cycles. The reaction system and program were the same as those in Table 7. The Mtu ΔI-CM full-length genes with saturated mutations at both H73 and T158 were obtained, upstream and downstream of which were respectively provided with EcoRI and HindIII enzyme recognition sites. The gene was subjected to DNA gel purification, EcoRI and HindIII enzymes were used for double enzyme digestion, then the gene was ligated to the vector pET30(a)-CFP-YFP after double enzyme digestion by the same endonuclease and dephosphorylation, and meanwhile, a ligation reaction without adding double digested genes was used as a negative control (control of vector self-ligation) to obtain target and control ligation products. The ligation products were transformed into E. coli BL21(DE3) to obtain a CASTing library of Mtu ΔI-CM at H73 and T158.

TABLE 12

Quantification of Single Site Mutation Strain in $L_6$KD-I-GLP1 System

| Variants | in vivo Cleavage Ratio[a] | Aggregate Yield (μg/mg cell wet weight)[b] | in vitro Cleavage Efficiency[c] | Protein of Interest Yield (μg/mg cell wet weight)[b] | Advantage[d] |
|---|---|---|---|---|---|
| T158S | 31% | 56.6 | 83% | 2.99 | 230% |
| H73V | 42% | 43.9 | 85% | 2.2 | 140% |
| H73Y | 35% | 58.2 | 89% | 3.92 | 330% |
| K74N | 54% | 31.9 | 82% | 1.57 | 70% |
| E154S | 53% | 38.7 | 86% | 1.34 | 50% |
| Mtu ΔI-CM | 68% | 24.4 | 85% | 0.91 | template |

[a]Percentage of in vivo cleavage, i.e., premature cleavage efficiency of intein, was defined as the mass ratio of the cleaved fusion protein aggregates in vivo over the theoretical value of the fusion protein aggregates.
[b]Calculation was based on "when the concentration of bacterial solution at $OD_{600}$ is 2, the wet cell weight is 2.66 ± 0.99 mg/ml in LB medium".
[c] Cleavage efficiency was defined as the mass ratio of the cleaved fusion protein aggregates in vitro over the fusion protein aggregates actually obtained.
[d] Advantage was defined as (the yield of protein of interest from mutant strain – the yield of protein of interest from Mtu ΔI-CM)/the yield of protein of interest from Mtu ΔI-CM × 100%.

Example 8: Construction and Screening of Combinatorial Active-Site Saturation Testing Library The mutant strains at site H73 and T158 have good performance in the cSAT method. This example combines the two sites 73 and 158, hoping to further improve the performance of the Mtu ΔI-CM intein. Since the distance between H73 and T158 is 8.3 Å, the inventors speculate that there may be a synergistic effect between them. Therefore, used the combinatorial active-site saturation testing (CASTing) method developed by Reetz et al. on the basis of the SDSM method to build a combined library of H73 and T158. By using the Mtu ΔI-CM intein as the template and with the NDT degeneracy codon, 12 amino acids were simultaneously introduced at H73 and T158 to establish a CASTing library. Used pUC18-Mtu ΔI-CM plasmid as the template, and Mtu-up-73-158 and CAST-Mtu-down-73 in Table 13 as forward and reverse primers, and amplified the upstream

TABLE 13

Sequences of Primers Used in this Example

| SEQ ID NO: | Primer Name | Sequence[a] | Description |
|---|---|---|---|
| 41 | Mtu-up-73-158 | 5'-CCGGAATTCGCGCTGGCTGAAGGCACG-3' (EcoRI) | forward primers for the construction of combined library |
| 42 | CAST-Mtu-up-73 | 5'-GGCAACCCCGGATNDTAAAGTGCTGACGGAATATG-3' | overlapping PCR primers |
| 43 | CAST-Mtu- | 5'-TCCGTCAGCACTTTAHNATCC | introducing 12 |

TABLE 13-continued

Sequences of Primers Used in this Example

| SEQ ID NO: | Primer Name | Sequence [a] | Description |
|---|---|---|---|
|  | down-73 | GGGGTTGCCCACAGAATTGCAC-3' | amino acids at H73 |
| 44 | Mtu-down-73-158 | 5'-CCCAAGCTTGTTATGAACCAC AACGCCTTCCGCAACCAGAHNA TGCAGTTCTTCCACTTCCA-3' (HindIII) | reverse primers for the construction of combinatorial library, introducing 12 amino acids at T158 |

[a] Nucleotides bolded in the sequence are degenerate codons NDT and AHN. NDT, a degenerate codon used in the forward primers for combinatorial active-site saturated mutation, wherein D represents a mixture of three bases: A, T and G; AHN, a degenerate codon used in the reverse primers for combinatorial active-site saturated mutation, wherein H represents a mixture of three bases: C, A and T.

The combinatorial library of H73 and T158 was screened by an Infinite M200 microplate reader (TECAN, Zürich, Switzerland) using the screening procedure described in Example 5, and 540 colonies (six 96-well plates) were selected with a mutation coverage rate of 98%. Finally, obtained 6 combinatorial site mutant strains with reduced in vivo cleavage efficiency in the C-I-Y system but still capable of effective in vitro cleavage, namely, H73Y/T158V, H73V/T158S, H73V/T158C, H73V/T158N, H73S/T158N and H73C/T158S, wherein the mutant strain H73V/T158S is a combination of two single mutant strains (H73V and T158S) with better performance obtained by site-directed saturated mutation.

Example 9: Characterization of Combinatorial Site Mutant Strain in $L_6$KD-I-LipA System In this example, the selected 6 combinatorial site mutant strains were constructed into the $L_6$KD-I-LipA system to verify if they can also be used for polypeptide preparation efficiently. Refer to the construction of the $L_6$KD-I(mutant)-LipA system in Example 6 for construction method, and the primers used are shown in Table 8.

Figure 7:
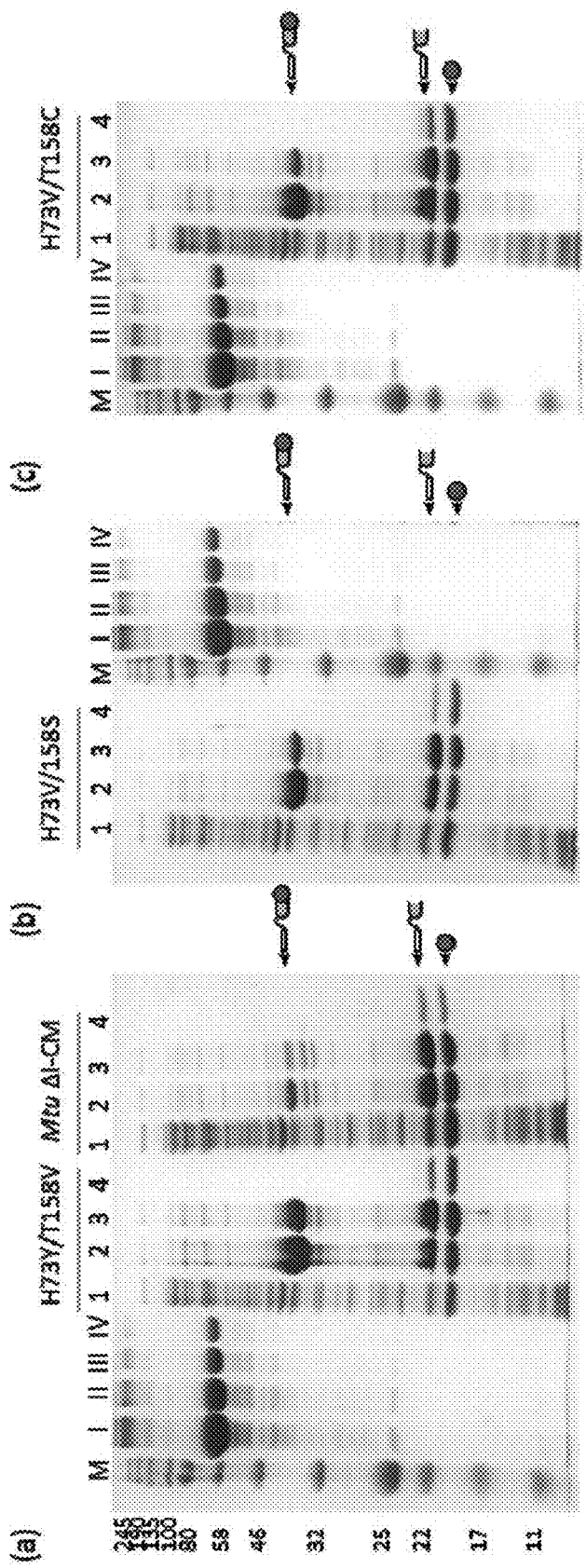
FIG. 7 shows the detection results of double mutant strains in the L6KD-I-LipA system, wherein (a), (b) and (c) are the results of variants H73Y/T158V, H73V/T158S and H73V/T158C in the L6KD-I-LipA system respectively; lane 1 is the supernatant of cell lysate; lane 2 is the precipitate of cell lysate; lane 3 is the precipitate after cleavage; lane 4 is the supernatant after cleavage; and lanes I, II, III and IV are BSA standards (at 1000, 500, 250 and 125 µg/ml, respectively).

*Escherichia coli* with recombinant plasmid pET30(a)-$L_6$KD-I(mutant)-GLP1 and a control strain were expressed and purified according to the method in Example 6, the obtained samples were analyzed by SDS-PAGE, and the detection results are shown in FIG. 7, and the quantitative results are shown in Table 14.

TABLE 14

Quantification of of Combinatorial Site Mutant Strain in $L_6$KD-I-LipA System

| Variants | Percentage of in vivo Cleavage [a] | Aggregate Yield [b] (μg/mg cell wet weight) | in vitro Cleavage Efficiency [c] | Aggregate Yield [b] (μg/mg cell wet weight) | Advantage [d] |
|---|---|---|---|---|---|
| H73Y/T158V | 27% | 57.7 | 71% | 9.3 | 94% |
| H73V/T158S | 36% | 36.5 | 74% | 8.2 | 71% |
| H73V/T158C | 45% | 41.5 | 84% | 8.2 | 71% |
| Mtu ΔI-CM | 87% | 9.7 | 85% | 4.8 | template |

[a] Percentage of in vivo cleavage, i.e., premature cleavage efficiency of intein, was defined as the mass ratio of the cleaved fusion protein aggregates in vivo over the theoretical value of the fusion protein aggregates.
[b] Calculation was based on "when the concentration of bacterial solution at $OD_{600}$ is 2, the wet cell weight is 2.66 ± 0.99 mg/ml in LB medium".
[c] Cleavage efficiency was defined as the mass ratio of the cleaved fusion protein aggregates in vitro over the fusion protein aggregates actually obtained.
[d] Advantage was defined as (the yield of protein of interest from mutant strain − the yield of protein of interest from Mtu ΔI-CM)/the yield of protein of interest from Mtu ΔI-CM × 100%.

The in vivo cleavage ratio of the fusion protein of mutant strain H73Y/T158V was reduced from 87% to 27%, which was the lowest among all obtained mutant strains, resulting in a 94% increase in LipA yield; and the in vivo cleavage ratio of the fusion protein of the mutant strain H73V/T158S was reduced from 87% to 36%, increasing LipA yield by 71%. However, the in vitro cleavage efficiency of the two mutant strains was slightly decreased. The in vivo cleavage ratio of the fusion protein of the mutant strain H73V/T158C was reduced from 87% to 45%, increasing LipA yield by 71%. The other 3 mutant strains were not as effective as the previous single site mutant strains, so they will not be constructed into the $L_6$KD-I-GLP1 system for verification.

Embodiment 10: Characterization of Combinatorial Site Mutant Strain in $L_6$KD-I-GLP1 System In this example, the selected 3 combinatorial site mutant strains were constructed into the $L_6$KD-I-GLP1 system to verify if they can also be used for polypeptide preparation efficiently. Refer to the construction of the $L_6$KD-I(mutant)-LipA system in Example 6 for construction method, and the primers used are shown in Table 11.

*Escherichia coli* with recombinant plasmid pET30(a)-$L_6$KD-I(mutant)-GLP1 and a control strain were expressed and purified according to the method in Example 6, the obtained samples were analyzed by SDS-PAGE, and the detection results are shown in FIG. 8. The quantitative results are shown in Table 15.

Similarly, the three combinatorial site mutant strains can also reduce the in vivo cleavage ratio of the $L_6$KD-I-GLP1 system to various degrees and improve the GLP-1 yield. The in vivo cleavage ratio of the fusion protein of the mutant strain H73Y/T158V was reduced from 68% to 18%, but the in vitro cleavage efficiency was greatly reduced from 85% to 48%, thus the yield of GLP-1 was only increased by 41% compared with the original system. However, the in vitro cleavage efficiency of the mutant strain in the $L_6$KD-I-LipA system was only slightly decreased (as shown in Table 15). The in vivo cleavage ratio of the fusion protein of the mutant strain H73V/T158S was reduced from 68% to 21%, increasing GLP-1 yield by 3.8-fold. The in vivo cleavage ratio of the fusion protein of the mutant strain H73V/T158C was reduced from 68% to 25%, increasing GLP-1 yield by 3.4-fold. Although the in vitro cleavage efficiency of mutant strain H73Y/T158V was decreased in this system, like in the $L_6$KD-I-LipA system, the in vivo cleavage efficiency of mutant strain H73Y/T158V was the lowest among all the obtained mutants, which was lower than that of the combinatorial mutant strain H73V/T158S of two selected mutant strains with better efficiency obtained by site-specific saturated mutation, indicating that there was indeed a certain degree of synergy effect between 73 and 158 sites, and showing the effectiveness of site combination using the combinatorial active-site saturation testing method.

TABLE 15

Quantification of Single Site Mutant Strain in $L_6$KD-I-GLP1 System

| Variants | Percentage of in vivo cleavage [a] | Aggregate Yield (μg/mg wet cell weight)[b] | in vitro Cleavage Efficiency [c] | Target Protein Yield (μg/mg wet cell weight)[b] | Advantage [d] |
|---|---|---|---|---|---|
| H73Y/T158V | 18% | 64.1 | 48% | 1.28 | 41% |
| H73V/T158S | 21% | 61.2 | 80% | 4.38 | 380% |
| H73V/T158C | 25% | 59.1 | 85% | 4.03 | 340% |
| Mtu ΔI-CM | 68% | 24.4 | 85% | 0.91 | template |

[a] Percentage of in vivo cleavage, i.e., premature cleavage efficiency of intein, was defined as the mass ratio of the cleaved fusion protein aggregates in vivo over the theoretical value of the fusion protein aggregates.
[b] Calculation was based on "when the concentration of bacterial solution at $OD_{600}$ is 2, the wet cell weight is 2.66 ± 0.99 mg/ml in LB medium".
[c] Cleavage efficiency was defined as the mass ratio of the cleaved fusion protein aggregates in vitro over the fusion protein aggregates actually obtained.
[d] Advantage was defined as (the yield of protein of interest from mutant strain – the yield of protein of interest from Mtu ΔI-CM)/the yield of protein of interest from Mtu ΔI-CM × 100%.

Those skilled in the art will understand that variations and modifications of the invention described herein other than those explicitly described are permissible. It should be understood that the present invention includes all such variations and modifications. The present invention also includes all steps, features, compositions and compounds mentioned or indicated individually or jointly in the specification, as well as any and all combinations, or any two or more of said steps or features.

```
Sequence Listing
Mtu ΔI-CM intein
                                                        SEQ ID NO: 1
ALAEGTRIFDPVTGTTHRIEDVVDGRKPIHVVAAAKDGTLHARPVVSWFDQGTRDVI

GLRIAGGAILWATPDHKVLTEYGWRAAGELRKGDRVAQPRRFDGFGDSAPIPARV

QALADALDDKFLHDMLAEELRYSVIREVLPTRRARTFGLEVEELHTLVAEGVVVHN

Mtu ΔI-CM intein variant H73Y
                                                        SEQ ID NO: 2
ALAEGTRIFDPVTGTTHRIEDVVDGRKPIHVVAAAKDGTLHARPVVSWFDQGTRDVI

GLRIAGGAILWATPDYKVLTEYGWRAAGELRKGDRVAQPRRFDGFGDSAPIPARV

QALADALDDKFLHDMLAEELRYSVIREVLPTRRARTFGLEVEELHTLVAEGVVVHN

Mtu ΔI-CM intein variant H73V
                                                        SEQ ID NO: 3
ALAEGTRIFDPVTGTTHRIEDVVDGRKPIHVVAAAKDGTLHARPVVSWFDQGTRDVI

GLRIAGGAILWATPDVKVLTEYGWRAAGELRKGDRVAQPRRFDGFGDSAPIPARV

QALADALDDKFLHDMLAEELRYSVIREVLPTRRARTFGLEVEELHTLVAEGVVVHN

Mtu ΔI-CM intein variant K74N
                                                        SEQ ID NO: 4
ALAEGTRIFDPVTGTTHRIEDVVDGRKPIHVVAAAKDGTLHARPVVSWFDQGTRDVI

GLRIAGGAILWATPDHNVLTEYGWRAAGELRKGDRVAQPRRFDGFGDSAPIPARV
```

-continued

QALADALDDKFLHDMLAEELRYSVIREVLPTRRARTFGLEVEELHTLVAEGVVVHN

Mtu ΔI-CM intein variant E154S

SEQ ID NO: 5

ALAEGTRIFDPVTGTTHRIEDVVDGRKPIHVVAAAKDGTLHARPVVSWFDQGTRDVI
GLRIAGGAILWATPDHKVLTEYGWRAAGELRKGDRVAQPRRFDGFGDSAPIPARV
QALADALDDKFLHDMLAEELRYSVIREVLPTRRARTFGLEVSELHTLVAEGVVVHN

Mtu ΔI-CM intein variant T158S

SEQ ID NO: 6

ALAEGTRIFDPVTGTTHRIEDVVDGRKPIHVVAAAKDGTLHARPVVSWFDQGTRDVI
GLRIAGGAILWATPDHKVLTEYGWRAAGELRKGDRVAQPRRFDGFGDSAPIPARV

QALADALDDKFLHDMLAEELRYSVIREVLPTRRARTFGLEVEELHSLVAEGVVVHN

Mtu ΔI-CM intein variant H73Y and T158V

SEQ ID NO: 7

ALAEGTRIFDPVTGTTHRIEDVVDGRKPIHVVAAAKDGTLHARPVVSWFDQGTRDVI

GLRIAGGAILWATPDYKVLTEYGWRAAGELRKGDRVAQPRRFDGFGDSAPIPARV

QALADALDDKFLHDMLAEELRYSVIREVLPTRRARTFGLEVEELHVLVAEGVVVHN

Mtu ΔI-CM intein variant H73V and T158S

SEQ ID NO: 8

ALAEGTRIFDPVTGTTHRIEDVVDGRKPIHVVAAAKDGTLHARPVVSWFDQGTRDVI

GLRIAGGAILWATPDVKVLTEYGWRAAGELRKGDRVAQPRRFDGFGDSAPIPARV

QALADALDDKFLHDMLAEELRYSVIREVLPTRRARTFGLEVEELHSLVAEGVVVHN

Mtu ΔI-CM intein variant H73V and T158C

SEQ ID NO: 9

ALAEGTRIFDPVTGTTHRIEDVVDGRKPIHVVAAAKDGTLHARPVVSWFDQGTRDVI

GLRIAGGAILWATPDVKVLTEYGWRAAGELRKGDRVAQPRRFDGFGDSAPIPARV

QALADALDDKFLHDMLAEELRYSVIREVLPTRRARTFGLEVEELHCLVAEGVVVHN

PT linker amino acid sequence

SEQ ID NO: 10

PTPPTTPTPPTTPTPTP

Mtu ΔI-CM intein variant H73Y nucleotide sequence

SEQ ID NO: 11

1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATTATA AAGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGG AAGAACTGCA TACCCTGGTT

481 GCGGAAGGCG TTGTGGTTCA TAAC

Mtu ΔI-CM intein variant H73V nucleotide sequence

SEQ ID NO: 12

1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATGTGA AAGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

```
361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGG AAGAACTGCA TACCCTGGTT

481 GCGGAAGGCG TTGTGGTTCA TAAC
```

Mtu ΔI-CM intein variant K74N nucleotide sequence

SEQ ID NO: 13
```
  1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATCATA ATGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGG AAGAACTGCA TACCCTGGTT

481 GCGGAAGGCG TTGTGGTTCA TAAC
```

Mtu ΔI-CM intein variant E154S nucleotide sequence

SEQ ID NO: 14
```
  1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATCATA AGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGA GTGAACTGCA TACCCTGGTT

481 GCGGAAGGCG TTGTGGTTCA TAAC
```

Mtu ΔI-CM intein variant T158S nucleotide sequence

SEQ ID NO: 15
```
  1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATCATA AGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGG AAGAACTGCA TTCTCTGGTT

481 GCGGAAGGCG TTGTGGTTCA TAAC
```

Mtu ΔI-CM intein variant H73Y and T158V nucleotide sequence

SEQ ID NO: 16
```
  1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATTATA AGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC
```

-continued

```
421 CTGCCGACCC GTCGCGCCCG CACGTTTGGT CTGGAAGTGG AAGAACTGCA TGTTCTGGTT

481 GCGGAAGGCG TTGTGGTTCA TAAC
```

Mtu ΔI-CM intein variant H73V and T158S nucleotide sequence
SEQ ID NO: 17

```
  1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATGTTA AGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGG AAGAACTGCA TAGTCTGGTT

481 GCGGAAGGCG TTGTGGTTCA TAAC
```

Mtu ΔI-CM intein variant H73V and T158C nucleotide sequence
SEQ ID NO: 18

```
  1 GCGCTGGCTG AAGGCACGCG CATTTTTGAT CCGGTCACGG GCACGACGCA CCGCATTGAA

61 GATGTTGTTG ATGGCCGCAA GCCGATTCAT GTGGTTGCGG CCGCAAAAGA TGGCACCCTG

121 CACGCCCGTC CGGTCGTGAG TTGGTTTGAT CAGGGTACGC GTGACGTCAT TGGTCTGCGT

181 ATCGCGGGCG GTGCAATTCT GTGGGCAACC CCGGATGTTA AGTGCTGAC GGAATATGGC

241 TGGCGTGCTG CGGGTGAACT GCGTAAGGGT GACCGTGTTG CACAGCCGCG TCGCTTTGAT

301 GGCTTCGGTG ACAGCGCACC GATTCCGGCT CGCGTTCAAG CCCTGGCAGA TGCTCTGGAT

361 GACAAGTTCC TGCACGACAT GCTGGCGGAA GAACTGCGTT ACTCTGTTAT CCGCGAAGTC

421 CTGCCGACCC GTCGCGCCCG CACGTTTGGT CTGGAAGTGG AAGAACTGCA TTGTCTGGTT

481 GCGGAAGGCG TTGTGGTTCA TAAC
``` primer N-Mtu
SEQ ID NO: 19
5'-CCGGAATTCGCGCTGGCTGAAGGCACGCGCATTT-3' primer Mtu-down-positive-FRET
SEQ ID NO: 20
5'-CCCAAGCTTGTTATGAACCACAACGCCTTCCGCAACCAG-3' primer Mtu-down-negative-FRET
SEQ ID NO: 21
5'-CCCAAGCTTGGCATGAACCACAACGCCTTCCGCAACCAG-3' primer Mtu-down-E152
SEQ ID NO: 22
5'-CCCAAGCTTGTTATGAACCACAACGCCTTCCGCAACCAGGGTATGCAGTTCT
TCCACMNNCAGACCAAACGTGCG-3' primer Mtu-down-E154
SEQ ID NO: 23
5'-CCCAAGCTTGTTATGAACCACAACGCCTTCCGCAACCAGGGTATGCAGTTCM
NNCACTTCCAGACC-3' primer Mtu-down-E155
SEQ ID NO: 24
5'-CCCAAGCTTGTTATGAACCACAACGCCTTCCGCAACCAGGGTATGCAGMNNT
TCCACTTCCAGACC-3' primer Mtu-down-T158
SEQ ID NO: 25
5'-CCCAAGCTTGTTATGAACCACAACGCCTTCCGCAACCAGMNNATGCAGTTCT
TCCA-3'

```
primer Mtu-up-H73                                       SEQ ID NO: 26
5'-GGCAACCCCGGATNNKAAAGTGCTGACGGAATATG-3' primer Mtu-down-H73                                     SEQ ID NO: 27
5'-TCCGTCAGCACTTTMNNATCCGGGGTTGCCCACAGAATTGCAC-3' primer Mtu-up-K74                                       SEQ ID NO: 28
5'-GGCAACCCCGGATCATNNKGTGCTGACGGAATATGGCTGGCGTG-3' primer Mtu-down-K74                                     SEQ ID NO: 29
5'-TATTCCGTCAGCACMNNATGATCCGGGGTTGCCCACAGAATTG-3' primer C-Mtu                                            SEQ ID NO: 30
5'-CCCAAGCTTGTTATGAACCACAACGCCTTCCGCAACCAG-3' primer Mtu-LipA-up                                      SEQ ID NO: 31
5'-TTGTGGTTCATAACCACCATCACCATCACCACCCCAC-3' primer Mtu-LipA-down                                    SEQ ID NO: 32
5'-GATGGTGATGGTGGTTATGAACCACAACGCCTTCCGCAA-3' primer Mtu-LipA-negative-up                             SEQ ID NO: 33
5'-TTGTGGTTCATGCCCACCATCACCATCACCACCCCAC-3' primer Mtu-LipA-negative-down                           SEQ ID NO: 34
5'-GTGATGGTGATGGTGGGCATGAACCACAACGCCTTCCGCAA-3' primer C-LipA                                           SEQ ID NO: 35
5'-AGTCTACTCGAGTCAATTCGTATTCTGGCCCCCGCCGTTC-3' primer Mtu-GLP1-up                                      SEQ ID NO: 36
5'-GTTGTGGTTCATAACCATGCAGAAGGCACCTTTACCA-3' primer Mtu-GLP1-down                                    SEQ ID NO: 37
5'-GTGCCTTCTGCATGGTTATGAACCACAACGCCTTCCGCAACC-3' primer Mtu-GLP1-negative-up                             SEQ ID NO: 38
5'-GCGTTGTGGTTCATGCCCATGCAGAAGGCACCTTTACCA-3' primer Mtu-GLP1-negative-down                           SEQ ID NO: 39
5'-GTGCCTTCTGCATGGGCATGAACCACAACGCCTTCCGCAACC-3' primer C-GLP1                                           SEQ ID NO: 40
5'-ATCTGACTCGAGTCAACCACGACCTTTAACCAGCC-3' primer Mtu-up-73-158                                    SEQ ID NO: 41
5'-CCGGAATTCGCGCTGGCTGAAGGCACG-3' primer CAST-Mtu-up-73                                   SEQ ID NO: 42
5'-GGCAACCCCGGATNDTAAAGTGCTGACGGAATATG-3' primer CAST-Mtu-down-73                                 SEQ ID NO: 43
5'-TCCGTCAGCACTTTAHNATCCGGGGTTGCCCACAGAATTGCAC-3' primer Mtu-down-73-158                                  SEQ ID NO: 44
5'-CCCAAGCTTGTTATGAACCACAACGCCTTCCGCAACCAGAHNATGCAGTTCTT
CCACTTCCA-3'

18A amino acid sequence                                 SEQ ID NO: 45
DWLKAFYDKVAEKLKEAF
```

```
ELK16 amino acid sequence
                                                    SEQ ID NO: 46
LELELKLKLELELKLK L6KD amino acid sequence
                                                    SEQ ID NO: 47
LLLLLLKD EFR8 amino acid sequence
                                                    SEQ ID NO: 48
FEFRFEFR EFK8 amino acid sequence
                                                    SEQ ID NO: 49
FEFKFEFK lipase LipA amino acid sequence
                                                    SEQ ID NO: 50
HHHHHHPTPMAEHNPVVMVHGIGGASFNFAGIKSYLVSQGWSRDKLYAVDFWDKT

GTNYNNGPVLSRFVQKVLDETGAKKVDIVAHSMGGANTLYYIKNLDGGNKVANVVT

LGGANRLTTGKALPGTDPNQKILYTSIYSSADMIVMNYLSRLDGARNVQIHGVGHIGL

LYSSQVNSLIKEGLNGGGQNTN

GLP1 amino acid sequence
                                                    SEQ ID NO: 51
HAEGTFTSDVSSYLEGQAAKEFIAWLVKGRG lipase LipA nucleotide sequence
                                                    SEQ ID NO: 52
CACCATCACCATCACCACCCCACCCCTATGGCTGAACACAATCCAGTCGTTATGG

TTCACGGTATTGGAGGGGCATCATTCAATTTTGCGGGAATTAAGAGCTATCTCGTA

TCTCAGGGCTGGTCGCGGGACAAGCTGTATGCAGTTGATTTTTGGGACAAGACA

GGCACAAATTATAACAATGGACCGGTATTATCACGATTTGTGCAAAAGGTTTTAGA

TGAAACGGGTGCGAAAAAAGTGGATATTGTCGCTCACAGCATGGGGGGCGCGA

ACACACTTTACTACATAAAAAATCTGGACGGCGGAAATAAAGTTGCAAACGTCGT

GACGCTTGGCGGCGCGAACCGTTTGACGACAGGCAAGGCGCTTCCGGGAACA

GATCCAAATCAAAAGATTTTATACACATCCATTTACAGCAGTGCCGATATGATTGTC

ATGAATTACTTATCAAGATTAGATGGTGCTAGAAACGTTCAAATCCATGGCGTTGG

ACACATCGGCCTTCTGTACAGCAGCCAAGTCAACAGCCTGATTAAAGAAGGGCT

GAACGGCGGGGGCCAGAATACGAAT

GLP1 nucleotide sequence
                                                    SEQ ID NO: 53
CATGCAGAAGGCACCTTTACCAGCGATGTTAGCAGCTATCTGGAAGGTCAGGCA

GCAAAAGAATTTATTGCATGGCTGGTTAAAGGTCGTGGT
```

---

What is claimed is that:

1. An isolated fusion protein comprising:
a polypeptide which is a variant of Mtu ΔI-CM intein, wherein the Mtu ΔI-CM intein has an amino acid sequence set forth in SEQ ID NO:1,
a purification tag, and
a molecule of interest,
wherein the purification tag is located at the N terminus of the polypeptide and the molecule of interest is located at the C terminus of the polypeptide,
wherein the polypeptide comprises an amino acid sequence:
   i) selected from a group consisting of SEQ ID NO:2, SEQ ID NO:3, SEQ ID NO:4, SEQ ID NO:5, SEQ ID NO:6, SEQ ID NO:7, SEQ ID NO:8 and SEQ ID NO:9; or
   ii) having at least 90% sequence identity with SEQ ID NO:1 and comprising one or more amino acid substitutions selected from the group consisting of H73Y, H73V, K74N, E154S, T158V, T158C and T158S positions of SEQ ID NO:1; and
wherein comparing with the Mtu ΔI-CM intein of SEQ ID NO:1, the polypeptide has reduced C-terminal cleavage efficiency at a first pH value in the range of 7.2-8.5 and similar or increased C-terminal cleavage efficiency at a second pH value in the range of 5.5-6.8, and the N-terminal cleavage activity of the polypeptide remains silenced.

2. The fusion protein according to claim 1, wherein the amino acid substitution is selected from a group consisting of:
H73Y and T158V;
H73V and T158S; and
H73V and T158C.

3. The fusion protein according to claim 1, wherein the purification tag is linked to the N terminus of the polypeptide through a spacer.

4. The fusion protein according to claim 3, wherein the spacer comprises a sequence set forth in SEQ ID NO:10.

5. The fusion protein according to claim 1, wherein the purification tag is an amphipathic self-assembling short peptide.

6. The fusion protein according to claim 1, wherein the molecule of interest is a peptide segment, which is 20, 50, 70, 100, 150, 200, 250, 300, 350, 400, 450 or 500 amino acid residues in length, or any length in between any two lengths stated above.

7. A method for producing a molecule of interest, comprising the steps of:
(a) cultivating host cells comprising a polynucleotide encoding the fusion protein of claim 1 to express said fusion protein;
(b) disrupting the host cells and recovering the fusion protein produced in step (a) at the first pH value in the range of 7.2-8.5;
(c) cleaving the fusion protein at the second pH value in the range of 5.5-6.8 to release the molecule of interest; and
(d) recovering the molecule of interest.

8. A method for purifying a molecule of interest from a sample, comprising the steps of:
(a) providing a sample containing the fusion protein of claim 1;
(b) collecting the fusion protein by the purification tag;
(c) adjusting pH value of a solution containing the fusion protein collected from step (b) such that the molecule of interest is cleaved from the fusion protein, wherein the adjusting pH value comprises adjusting the pH from the first pH value to the second pH value, wherein the first pH value is a pH of 7.2-8.5, and the second pH value is a pH of 5.5-6.8; and
(d) recovering the molecule of interest.

9. The method according to claim 8, wherein the purification tag is an amphipathic self-assembling short peptide.

10. The method according to claim 8, wherein the molecule of interest is a peptide segment, which is 20, 50, 70, 100, 150, 200, 250, 300, 350, 400, 450 or 500 amino acid residues in length, or any length in between any two lengths stated above.

* * * * *